United States Patent
Herrmann et al.

(10) Patent No.: US 10,285,939 B2
(45) Date of Patent: May 14, 2019

(54) MEANS AND METHODS FOR OCULAR DRUG DELIVERY

(71) Applicant: Eberhard Karls Universität Tübingen Medizinische Fakultät, Tübingen (DE)

(72) Inventors: Andreas Herrmann, Groningen (NL); Jan Willem De Vries, Groningen (NL); Martin Stephan Spitzer, Tübingen (DE); Sven Oliver Schnichels, Tübingen (DE)

(73) Assignee: Eberhard Karls Universität Tübingen Medizinische Fakultät, Tübingen (DE)

( * ) Notice: Subject to any disclaimer, the term of this patent is extended or adjusted under 35 U.S.C. 154(b) by 45 days.

(21) Appl. No.: 15/022,219

(22) PCT Filed: Sep. 17, 2014

(86) PCT No.: PCT/NL2014/050634
§ 371 (c)(1),
(2) Date: Mar. 16, 2016

(87) PCT Pub. No.: WO2015/041520
PCT Pub. Date: Mar. 26, 2015

(65) Prior Publication Data
US 2016/0346203 A1   Dec. 1, 2016

(30) Foreign Application Priority Data

Sep. 17, 2013   (EP) ..................................... 13184850

(51) Int. Cl.
| | | |
|---|---|---|
| *A61K 9/107* | (2006.01) |
| *A61K 31/557* | (2006.01) |
| *A61K 31/7036* | (2006.01) |
| *A61K 47/26* | (2006.01) |
| *A61K 9/00* | (2006.01) |
| *A61K 47/69* | (2017.01) |

(52) U.S. Cl.
CPC .......... *A61K 9/1075* (2013.01); *A61K 9/0048* (2013.01); *A61K 9/107* (2013.01); *A61K 31/557* (2013.01); *A61K 31/7036* (2013.01); *A61K 47/26* (2013.01); *A61K 47/6907* (2017.08)

(58) Field of Classification Search
CPC .. A61K 9/1075; A61K 9/0048; A61K 47/488; A61K 47/26; A61K 31/7036; A61K 31/557
USPC ....................................................... 514/44 R
See application file for complete search history.

(56) References Cited

U.S. PATENT DOCUMENTS

2009/0226531 A1* 9/2009 Lyons .................. A61K 9/0048
424/501

FOREIGN PATENT DOCUMENTS

| WO | WO-2009021728 A2 | 2/2009 |
| WO | WO-2012173477 A1 | 12/2012 |
| WO | WO-2015041520 A1 | 3/2015 |

OTHER PUBLICATIONS

Glossary of medical education terms, Institute of International Medical Education. http://www.iime.org/glossary.htm Accessed in Mar. 2013. (Year: 2013).*
Bucolo et al. Pharmacological management of ocular hypertension: current approaches and future prospective. Current Opinion in Pharmacology 2013, 13:50-55. Available online Oct. 12, 2012. (Year: 2012).*
"International Application Serial No. PCT/NL2014/050570, International Preliminary Report on Patentability dated Sep. 24, 2015", 20 pgs, (2015).
"International Application Serial No. PCT/NL2014/050634, International Search Report dated Jan. 8, 2015", 4 pgs, (2015).
"International Application Serial No. PCT/NL2014/050634, International Written Opinion dated Jan. 8, 2015", 4 pgs, (2015).
Yeung, Karent K, et al., "Bacterial Conjuntivitis (Pink Eye) Medication", URL: https://emedicine.medscape.com/article/1191730-medication, (accessed May 17, 2018), 1 pgs.

* cited by examiner

*Primary Examiner* — Yih-Horng Shiao
(74) *Attorney, Agent, or Firm* — Schwegman Lundberg & Woessner, P.A.

(57) ABSTRACT

The invention relates to compositions and methods that utilize polymeric nanoparticles to deliver a therapeutic compound to ocular cells or ocular tissue. Provided is a drug-loaded micelle comprising self-assembled amphiphilic biopolymers, such as hydrophobically modified nucleic acids or polypeptides, for use as ophthalmic drug delivery system. Also provided are ophthalmic compositions and methods for preventing or treating an ophthalmic disease.

20 Claims, 11 Drawing Sheets

Figures 1A, 1B:
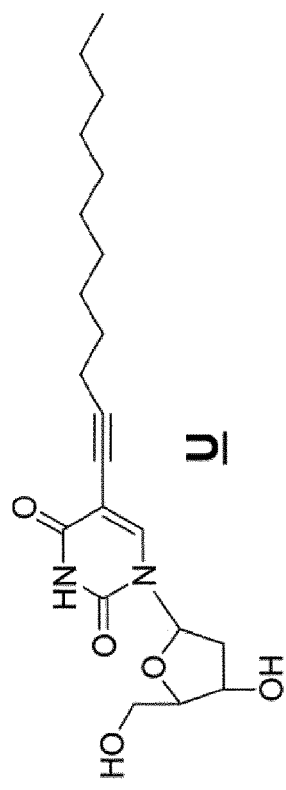

| Name | Sequence (5' → 3') | Lipid modified bases (# (%)) |
|---|---|---|
| U2T-12 | UUTGGCGGATTC | 2 (17) |
| U4T-12 | UUUUGCGGATTC | 4 (33) |
| U4T-18 | UUUUGCGGATTCGTCTGC | 4 (22) |
| U6T-12 | UUUUUUGGATTC | 6 (50) |
| U6T-20 | UUUUUUGCGGATTCGTCTGC | 6 (30) |
| U12R-36 | (UUUUGCGGATTC)$_3$ | 12 (33) |
| U20R-60 | (UUUUGCGGATTC)$_5$ | 20 (33) |

FIG. 2A

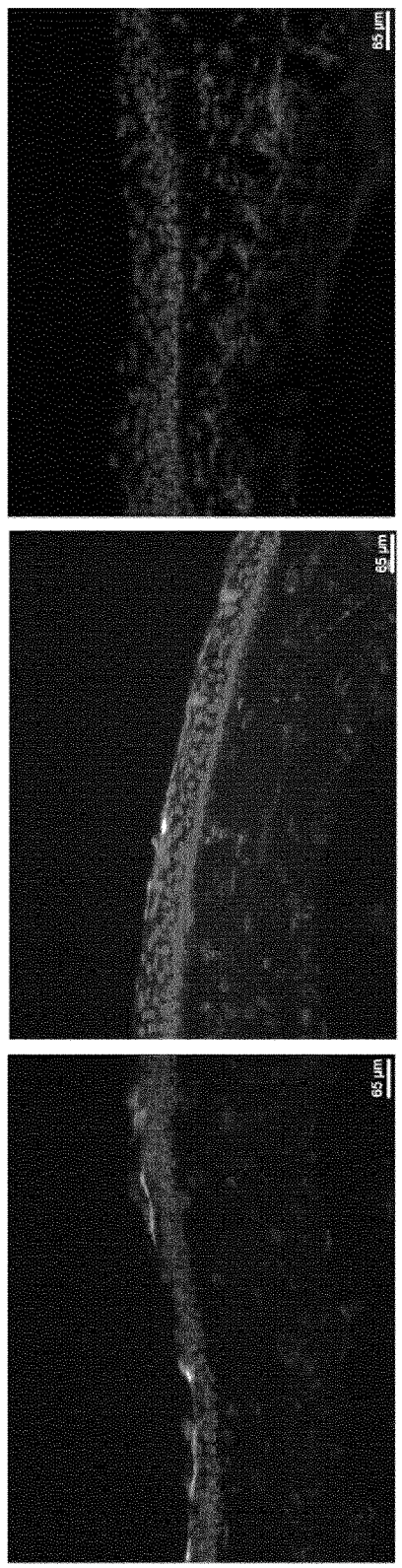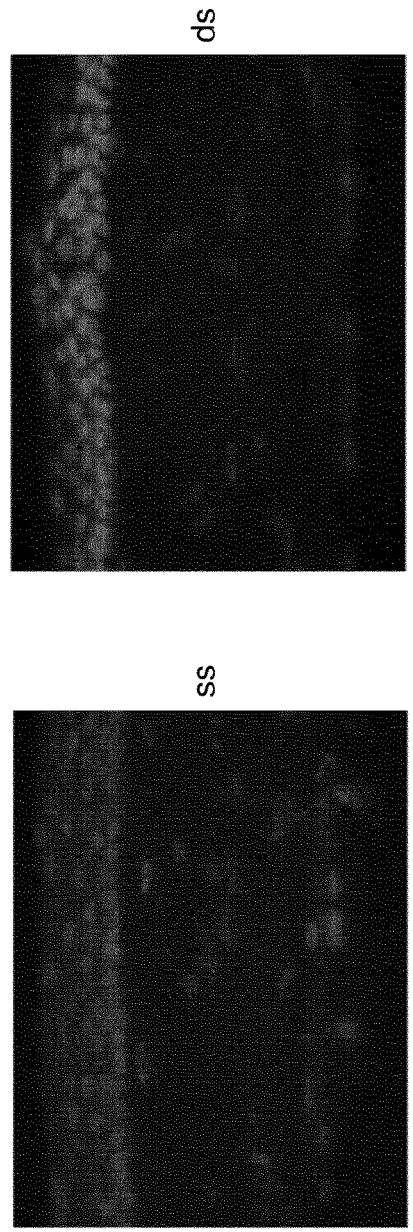
FIG. 2B
FIG. 2C

MEANS AND METHODS FOR OCULAR DRUG DELIVERY

PRIORITY APPLICATIONS

This application is a U.S. National Stage Filing under 35 U.S.C. 371 from International Application No. PCT/NL2014/050634, filed on 17 Sep. 2014, and published as WO 2015/041520 on 26 Mar. 2015, which claims the benefit of European Application No. 13184850.9, filed on 17 Sep. 2013; which applications and publication are incorporated herein by reference in their entirety.

The invention relates to topical ocular drug delivery compositions and methods for using the same. In particular, the present invention relates to compositions and methods that utilize polymeric nanoparticles to deliver a therapeutic compound to ocular cells or ocular tissue.

Ocular drug delivery is a major challenge because of unique barrier properties offered by nature to the eye as protective mechanism. The most commonly used topical route typically results in less than 5% bioavailability in the anterior segment eye tissue and less than 0.05% in the posterior segment eye tissues due in part to rapid clearance of drug from the ocular surfaces by blinking and tear drainage, and poor permeability across the cornea and conjunctiva. Topically applied drug molecules have access to the intraocular tissues by permeability across ocular barriers either by transporter mediated active transport or passive diffusion which include both paracellular and transcellular routes. Passive permeability of drugs across the cornea and conjunctiva is limited by inter alia, very tight epithelial junctions as well as the multilayers of the corneal and conjunctival epithelium.

Currently, treatment of most eye related diseases is done using eye drops. However, drug uptake is severely hindered by the tear fluid and eye lid movement. Also, due to poor permeability of drug molecules across the ocular barriers and rapid clearance from the ocular surface, frequent multiple eye drops are needed to maintain the therapeutically effective concentration in the target tissues. As such, very frequent administration of highly concentrated eye drops is necessary, causing poor compliance and substantial side effects.[1,2] The latter occur very frequently and can range from simple irritations to life threatening anaphylactic shocks in extreme cases.[3,4] Compliance is a very well-known and well-studied problem in medicine and in general only approximately 60% of all people are able to correctly follow medical advice when having to take eye drops three times a day.[5] Therefore, increasing the drug half-life time on the eye is an important goal for the improved treatment of eye diseases.

In the past, the effectiveness of eye drops has been slightly increased by changing the viscosity and composition of the drops. However, this results in very little improvement and causes reduced vision when the medicine is applied, which in turn leads to a lack of compliance.

Great efforts have been dedicated towards replacing eye drops with invasive drug depots like punctual plugs and implants. Unfortunately, these alternatives all require surgical interventions for installation and afterwards commonly provoke allergic reactions and occasionally eject spontaneously from the eye or may even be the source of a sight-threatening intraocular infection. One example is the bio-erodible implant from Pfizer/pSivida, currently in phase II clinical trials. The implant will be injected in the subconjunctival space and during degradation releases latanoprost over a period of several months. However, implants cause scar tissue and as such significantly increase the risk for failure of glaucoma surgery, which eventually is needed for most glaucoma patients.

Accordingly, the present inventors set out to develop improved means and methods for treating an ocular disease, in particular by improved drug delivery to ocular tissues. In particular, they aimed at providing a general drug delivery platform which significantly increases the adherence time of the drug in the eye and thus allows for a lower frequency of drug administration as compared to existing ophthalmic delivery systems.

It was surprisingly found that these goals could be met by modularly assembled nano-objects in the form of drug-loaded micelles comprising self-assembled amphiphilic biopolymers. For example, by employing microphase separation of amphiphilic DNA molecules, DNA nanoparticles (NPs) were generated that can easily be loaded with several kinds of drugs. Using this novel carrier system we are able to significantly increase the adherence time of the drug in the eye. As a consequence, a lower frequency of (topical) drug administration is feasible which is beneficial for the compliance and treatment of the patient. By increasing the duration time of the medication, a lower regime can be attained, resulting in an improved compliance. Moreover, due to the improved adherence, a lower drug concentration can be used, that drastically reduces systemic and local side effects as well as treatment costs. In addition, it gives the possibility to use medication that is currently harmful to apply. For example, drugs currently not in use due to their severe side effects could become utilized again.

Accordingly, the invention provides a drug-loaded micelle comprising self-assembled amphiphilic biopolymers, for use in a method of treating an ocular disease, e.g. as part of an ophthalmic drug delivery system. Preferably, the topical drug-loaded micelle comprising self-assembled amphiphilic biopolymers is used in a method for the topical treatment of an ocular disease.

As used herein, the term "amphiphilic biopolymer" refers to any substance having a hydrophilic moiety and a hydrophobic moiety which undergoes self assembly into a micelle under physiological conditions and wherein at least the hydrophilic moiety is based on a naturally occurring, body-own, polymer. Typically, the hydrophilic moiety is based on a polynucleotide or a hydrophilic polypeptide. Exploiting the nature of such biological molecules allows for surface functionalization, in particular drug-loading, in a highly specific and versatile manner.

The use of polymeric micelles in ocular drug delivery is known in the art. See for example Pepic et al. (2012, Chem. Biochem. Eng. Q. 26 (4) 365-377) providing a review on aqueous-based formulations of drug loaded polymeric micelles for use in ophthalmic drug delivery. Disclosed are various exemplary micellar systems, none of which is based on an amphiphile comprising a polynucleotide or polypeptide. Furthermore, all systems relate to hydrophobic drugs that are physically entrapped in the hydrophobic core of the micelle.

US2006/0110356 relates to an ophthalmic drug delivery system comprising administering a polymer micelle formed with a block copolymer comprising a hydrophilic polymer chain as a shell and a hydrophobic polymer chain as a core and incorporated a drug therein. The micelle is used to deliver the drug to a posterior tissue of an eyeball by intravenous injection, in particular for use in photodynamic therapy.

WO2009/021728 relates to selective drug targeting and discloses a targeted block copolymer micelle comprising an amphiphilic block copolymer consisting of a hydrophobic polymer attached to the a first nucleic acid which is hybridized with a second nucleic acid that is provided with a targeting unit capable of selectively binding to a specific cell type and/or tissue. Also disclosed is the covalent attachment of a hydrophilic drug via a cleavable linked to the second nucleic acid. WO2009/021728 is focussed on anti-cancer treatment by incorporating hydrophobic cytotoxic agents in the core and fails to teach or suggest use of the micelles as topical ophthalmic drug delivery platform.

The field of DNA nanotechnology[6] has progressed rapidly in the past decades and pristine DNA nanoobjects[7-9] and nanostructures composed of nucleic acids combined with other organic[10, 11] or inorganic[12] materials with a large diversity of predetermined 1D, 2D and 3D shapes are readily accessible. Hence various potential applications of these nanostructures in different areas such as biosensing[13-15], biocatalysis[16, 17], drug discovery[18] and nucleic acid delivery[19-23] have been pursued. All these examples take advantage of the programmable self-assembly properties and the shape persistence of the nucleic acids. In the field of drug delivery the same properties can be translated into well-defined nano-objects with full control over the spatial distribution and number of targeting or imaging units as well as the active compounds. These nanoparticles (NPs) were successfully employed for delivery of small molecule drugs[24-26] but demonstration of DNA carriers for low molecular weight actives in-vivo remains elusive. Another limitation of DNA-based vehicles is their restricted use only in anticancer therapy so far. Here we demonstrate the successful application of biopolymer-based nanoparticles for ophthalmic drug delivery.

In one embodiment of the invention, a micelle comprises as amphiphile a nucleic acid molecule provided at its 3' or 5' terminal hydroxyl with a hydrocarbon chain. The nucleic acid molecule can be single stranded DNA or RNA, or double stranded DNA/DNA, RNA/RNA or DNA/RNA. As used herein, the term "hydrocarbon chain" refers to branched and linear molecules essentially only comprising the elements hydrogen and carbon. In one aspect, the hydrocarbon chain is composed solely of hydrogen and carbon atoms. The hydrocarbon chain can be saturated or unsaturated. Saturated hydrocarbons (alkanes) are the simplest of the hydrocarbon species. They are composed entirely of single bonds and are saturated with hydrogen. Unsaturated hydrocarbons have one or more double or triple bonds between carbon atoms. Those with double bond are called alkenes. In one embodiment, the hydrocarbon chain is an alkyl chain of the general formula $C_nH_{2n+1}$.

A hydrocarbon chain present in an amphiphilic biopolymer at the 3' or 5' terminal hydroxyl according to the invention preferably comprises at least 14 C-atoms, more preferably at least 16 C-atoms to provide sufficient hydrophobic character to the amphiphile. There is no upper limit as to the chain length. However, for practical reasons the hydrocarbon chain typically contains up to about 80 C-atoms, preferably up to about 50 atoms. The hydrocarbon chain is preferably a linear alkyl. For example, good results were obtained with a C18, C20, C24, C28, C30, C34 or C40 hydrocarbon chain.

In one embodiment, the amphiphilic biopolymer is a nucleic acid molecule comprising at the 3' or 5' end with at least one hydrophobically-modified nucleotide which is modified at the nucleobase, ribose or phosphate group. At least one hydrophobically-modified nucleotide is for example modified at the nucleobase, ribose or phosphate group with a linear or branched aliphatic hydrocarbon chain. The nucleotide can be a naturally occurring nucleotide, like thymidine, uridine, adenosine, guanosine or cytidine, or a nucleotide analog, for example deoxyuridine or 2'-O-propargyl cytidine. The aliphatic hydrocarbon chain can be branched or not, and typically contains 6 to 30 C-atoms, preferably 10-24 C-atoms. Very good results were obtained with straight alkyl chains containing 12 to 20 carbons.

In one embodiment, the nucleotide is modified at the nucleobase. For example, provided are modified uracil phosphoramidites and micelles comprising them, wherein the nucleobase is provided with an aliphatic hydrocarbon chain of 6 to 30 C-atoms, preferably 10-24 C-atoms. Very good results were obtained with straight C10-C20 alkyl chains, for instance C12 or C18 alkyls. Exemplary amphiphiles of this type include U4T-12 and V4T-12 C18 exemplified herein below, which contain a C12 and C18 hydrocarbon chain, respectively.

In another embodiment, the nucleotide is modified at the phosphate group. In yet another embodiment, the nucleotide is modified at the ribose. For example, RNA can be modified at the 2'hydroxyl group with a long alkyl chain upon ester formation to provide an amphiphilic biopolymer whose degradation products are entirely natural compounds, i.e. nucleotides and fatty acids.

Preferably, the hydrophobic moiety comprises a stretch of at least 2, more preferably at least 3, contiguous hydrophobically-modified nucleotides. Contiguous hydrophobically-modified nucleotides can have the same or distinct hydrophobic groups, for example alkyl chains of different lengths. For example, by incorporation of several hydrophobically-modified 2'-deoxyuridines (U) into DNA strands amphiphiles are formed that self-assemble into micellar aggregates through microphase separation.

The resulting nanoparticles exhibit a corona of single stranded DNA that can be easily functionalized by hybridization. For the purpose of imaging we hybridized an oligonucleotide functionalized with a fluorophore. For drug loading, a DNA aptamer binding kanamycin B and a RNA aptamer binding neomycin B were extended at the 3' position with the complementary sequence of the DNA amphiphile. Watson-Crick base pairing of aminoglycoside complexed aptamers and DNA nanoparticles resulted in two antibiotic loaded nanocarrier systems.

A further aspect of the invention relates to drug-loaded micelles comprising self-assembled amphiphilic biopolymers, for use as (topical) ophthalmic drug delivery system, e.g. in the treatment of a disease and/or disorder in the ophthalmic field, wherein the amphiphilic biopolymer is a polypeptide comprising at its C- or N-terminus a hydrophobic moiety. Similar to what is described above for polynucleotide-based amphiphiles, the polypeptide can be provided with one or more hydrophobic polymer(s) or oligomer(s), like a hydrocarbon chain lipid. Alternatively, the polypeptide may contain at one of its termini one or more amino acid residues that are chemically modified with a hydrophobic moiety, like a linear or branched aliphatic hydrocarbon (e.g. alkyl) chain. In yet an alternative embodiment, a stretch of amino acids having a hydrophobic character is used to confer the polypeptide with amphipathic, self-assembling properties. Peptide-based self-assembling micelles are known in the art. For example, a review by Trent et al. (Soft Matter, 2011, 7, 9572) provides an overview of the various developments in relation to therapeutic and diagnostic application of soluble peptide amphiphile micelles. Cui et al. (Peptide Science, 2010, 94, 1) discuss the use of molecular self-assembly to produce peptide amphiphile nanostructures and their applications as therapeutic, for example for treating spinal cord injury, inducing angiogenesis and for hard tissue regeneration. However, the art is silent about the use of peptide-based micelles as (topical) ocular drug delivery platform in a method for preventing or treating an ophthalmic disease or disorder A micelle according to the invention can be loaded in different ways with one or more drugs. In one embodiment, the micelle comprises a hydrophobic drug which is enclosed in the hydrophobic core of the micelle. Alternatively, or additionally, the hydrophilic moiety of at least one amphiphile is provided with at least one drug, such that the drug is present essentially at the outer surface of the micelle. Thus, drug loading can be in the hydrophobic interior (core) of the micelle, at the hydrophilic exterior (surface) of the micelle, or both. In one aspect, both the core and the surface are provided with a drug. This system is particularly suitable to obtain a delivery system with a specific drug-release profile, for instance a rapid initial release from the surface, followed from a more sustained release from the core of the micelle. The drugs in the core and at the surface can be different or the same. Also, any combination of drugs can be loaded in the core and/or at the surface.

Drug-loading via the hydrophilic moiety of the self-assembling amphipathic biopolymer can be achieved via a covalent or non-covalent interaction. In one embodiment, the hydrophilic moiety is a first nucleic acid and a drug is attached to the hydrophilic moiety via a hybridized second nucleic acid that is provided with a drug. For example, a drug is covalently bound to said hybridized second nucleic acid. As is demonstrated herein below, it is also possible that a drug is bound to the hybridized second nucleic acid via an aptameric interaction. In one embodiment, a drug is bound via a DNA- or RNA-aptamer. In a specific aspect, the invention provides a drug-loaded micelle comprising self-assembled amphiphilic biopolymers for use as topical ophthalmic drug delivery system, wherein the amphiphilic biopolymer is a hydrophobically modified first nucleic acid sequence hybridized to a second nucleic acid sequence, the second nucleic acid sequence comprising a DNA- or RNA aptamer.

A person skilled in the art will be able to design a suitable aptamer sequence for a given drug of interest. See for example the review by Tan et al. (Trends in Biotechnology December 2011, Vol. 29, No. 12). One well-established selection process to identify and isolate aptamers with specific binding affinities is SELEX. See Mascini et al. (Angew. Chem. Int. Ed., 2012, 51, 1316-1332) or Stoltenburg et al. (Biomol. Eng., 2007, 24, 381-403) and references cited therein. The starting point for this in vitro selection is a combinatorial RNA or DNA library composed of $10^{14-15}$ single-stranded nucleic acids, each containing 20-40 nucleotides of random sequence. A starting library of nucleic acids is incubated with the target of interest. Molecules that bind to the target are partitioned from other sequences in the library. The bound sequences are then amplified repeatedly to generate an aptamer pool enriched in sequences that bind to the target protein. After several rounds of incubation, washing and amplification (usually eight to twelve), which are typically performed with increasing stringency, the selected ligands are sequenced and evaluated for their affinity to the target molecule. Aptamers are stable under a wide range of buffer conditions and resistant to harsh treatments. Aptamers can be isolated by a simple in vitro process for virtually any target, even those that are toxic or have low immunogenicity. Aptamers can be chemically synthesized, offering a wide variety of targeted modifications.

Specific aptamers for use in the present invention include those capable of binding a neamine-based aminoglycoside antibiotic, like neomycin or kanamycin. For example, in one specific embodiment the RNA sequence 5'-ggacugggcga-gaaguuuaguccgcuaauccgcaaaa-3' is used for surface loading a polynucleotide-based micelle with neomycin. In another specific embodiment, the DNA sequence 5'-TGGGGGTT-GAGGCTAAGCCGAT TGAATCCGCAAAA-3' is used to bind kanamycin. See also WO2012/173477.

Drug loading of a micelle that is based on peptide amphiphiles can also be achieved in a covalent or non-covalent manner. For example, a drug is attached directly to the hydrophilic end of the polypeptide using conventional chemistry. Preferably, the drug is conjugated to the amphiphile by a cleavable linker. The chemistry on cleavable linkers is known in the art, see for instance Leriche et al., Bioorgan. Med. Chem., 2012, 20, 571-582. As another example, the drug itself is a proteinaceous substance (e.g. a bioactive peptide), which is fused directly or via a (cleavable) spacer sequence to the hydrophilic part of the self-assembling amphiphilic polypeptide. Non-covalent drug loading is suitably performed via any type of proteinaceous drug binding moiety, such as a peptide-based aptamer. A naturally occurring drug-binding motif, or an engineered version thereof, can be fused directly or via a spacer sequence to the self-assembling polypeptide.

In a preferred aspect, an oligopeptide aptamer sequence is used for loading a drug onto a polypeptide-based micelle. As used herein, the term oligopeptide aptamer refers to any proteinaceous substance consisting of between about 5 and 120 amino acids, either in the L- or D-configuration, capable of binding the drug of interest. As used herein, the term "amino acid" encompasses both naturally occurring and (semi)-synthetic amino acid analogues. For example, one or more non-natural amino acid analogues can be incorporated into proteins by genetic engineering (C. C. Liu, P: G: Schultz, Ann. Rev. Biochem., 79, 413-44). Typically, a certain minimum size is needed to achieve high binding constants. In one embodiment, the oligopeptide aptamer consists of from 8-20 amino acids, preferably 10-18 amino acids, like 12, 13, 14, 15, 16, 17 or 18 amino acids.

Methods for selecting an oligopeptide aptamer are also known in the art. For example, it involves expressing a library of candidate oligopeptide aptamers in a recombinant host cell, and selecting at least one host cell expressing a desired aptamer and identifying the oligopeptide aptamer. In another embodiment, it comprises the screening of candidate peptides expressed on the cell surface of the host cell. See for example "Decorating microbes: surface display of proteins on *Escherichia coli*", Bloois E, Winter R T, Kolmar H, Fraaije M W, Trends in Biotechnology, Volume 29, Issue 2, 79-86, 10 Dec. 2010.

Another suitable method is phage display. Thereby, a library of random peptides is expressed in M13 phages followed by the selection of those phages displaying a peptide that can access and bind to an immobilized target drug compound. An oligopeptide aptamer can be selected by screening the host cell for the ability of the oligopeptide to modulate the biological activity of the drug compound. In a very specific embodiment, a peptide aptamer is capable of binding an aminoglycoside antibiotic, like neomycin. For example, the amino acid sequence GRFEED-IGSMRSGGGS or SQAMSTLEDHAE is fused to the amphiphile to allow for micelle loading with the drug neomycin. See also WO2012/173477 for oligopeptide aptamers capable of binding an aminoglycoside antibiotic.

Also provided is a drug-loaded micelle comprising self-assembled amphiphilic first nucleic acid molecules provided at the 3' or 5' end with a hydrophobic moiety and wherein at least one drug is attached to the first nucleic acid molecule via a hybridized second nucleic acid that is provided with a drug, preferably wherein the drug is bound to the hybridizing second nucleic acid via a DNA or RNA aptamer. In a specific aspect, the amphiphilic first nucleic acid molecules are provided at the 3' or 5' end with a stretch of at least 2, preferably at least 3, contiguous hydrophobically-modified nucleotides. For example, in one embodiment the micelles comprise amphiphilic nucleic acid molecules consisting of 10 to 20 nucleotides, wherein the hydrophobic moiety at the 3' or 5' end is formed by 2 to 6 consecutive hydrophobically modified nucleotides. Still more preferred, about 25 to 35% of the nucleotides of the first nucleic acid molecule are modified with a lipid. Such micelles were found to display a surprisingly fast and sustained adherence to the cornea. As a specific example, the nucleic acid molecule consists of 12 nucleotides, comprising a stretch of 4 nucleotides at the 3' or 5' end that are all lipid modified. As another specific example, the nucleic acid molecule consists of 20 nucleotides, comprising a stretch of 6 nucleotides at the 3' or 5' end that are all lipid modified.

Still further, there is provided a drug-loaded micelle comprising self-assembled amphiphilic nucleic acid molecules provided at the 3' or 5' end with a hydrophobic moiety and wherein at least one drug is attached to the nucleic acid molecule via a DNA or RNA aptamer, preferably via a hybridized second nucleic acid that is provided with an aptamer-bound drug. In a preferred embodiment, self-assembled amphiphilic nucleic acid molecules comprise at the 3' or 5' end at least one, preferably two or more, hydrophobically-modified nucleotide which is modified at the nucleobase, ribose or phosphate group.

As will be appreciated by the person skilled in the art, a micelle can be loaded with any drug or combination of drugs. In view of its advantageous therapeutic use in the ophthalmic field, the drug is preferably an ophthalmic drug, for example selected from the group consisting of anti-glaucoma agents, anti-angiogenesis agents, anti-infective agents, non-steroidal and steroidal anti-inflammatory agents, growth factors, immunosuppressant agents, anti-allergic agents, and any combination or pro-drug form thereof. Specific exemplary drugs for use in an ophthalmic drug delivery system of the invention include beta-blockers including timolol, betaxolol, levobetaxolol, carteolol, miotics including pilocarpine, carbonic anhydrase inhibitors, prostaglandins including latanoprost, bimatoprost, tafluprost, unoprostone and travoprost, seretonergics, muscarinics, dopaminergic agonists, adrenergic agonists including apraclonidine and brimonidine; anti-angiogenesis agents; anti-infective agents including anti-bacterial quinolones such as ciprofloxacin, and aminoglycosides such as tobramycin and gentamicin; and anti-viral agents including acyclovir, ganciclovir non-steroidal and anti-mykotic anti-parasitic drugs such as voriconazol or amphotericin B and steroidal and non-steroidal anti-inflammatory agents, such as dexamethasone, prednisolone, suprofen, diclofenac, ketorolac, rimexolone, and tetrahydrocortisol and cyclosporin A; growth factors, such as EGF; immunosuppressant agents including cyclosporins; and anti-allergic agents including olopatadine, ketotifen, levo-cabastine, naphazoline, nedocromil, azelastine, naphazoline and cromoglicic acid. In a specific aspect, the drug is an aminoglycoside antibiotic, such as neomycin or kanamycin.

Also provided is an ophthalmic composition comprising a drug-loaded micelle described herein above, and a suitable carrier. The ophthalmic composition preferably comprises at least one agent selected from the group consisting of pharmaceutically acceptable buffering agents, preservatives, non-ionic tonicity-adjusting agents, surfactants, solubilizing agents, stabilizing agents, comfort-enhancing agents, emollients, pH-adjusting agents and lubricants. The ophthalmic composition may, in addition to the one or more micelle-associated drug(s), further comprise at least one further ophthalmic drug, e.g. as "free" substance.

An ophthalmic composition according to the invention can be formulated in any manner that is suitable for delivery to the eye. For example, it is in the form of a solution, a gel or a suspension. In a further embodiment, it is formulated as an injectable. Preferred formulations include eye drops, degradable or non-degradable drug depots and injectable solutions.

An ophthalmic composition typically comprises ophthalmologically acceptable liquids. An ophthalmologically acceptable liquid includes a liquid formulated that is tolerable to a patient for topical ophthalmic use. Additionally, an ophthalmologically acceptable liquid could either be packaged for single use, or for multiple uses containing a preservative to prevent contamination. For ophthalmic application, solutions or medicaments may be prepared using a physiological saline solution as a major vehicle. Ophthalmic solutions may be maintained at a comfortable pH with an appropriate buffer system. The formulations may also contain conventional, pharmaceutically acceptable preservatives, stabilizers and surfactants.

An ophthalmologically acceptable liquid may include further demulcents or film forming materials. Examples of demulcents may include, but are not limited to polymers such as polyvinyl alcohol, povidone, hydroxypropyl methyl cellulose, poloxamers, carboxymethyl cellulose, hydroxyethyl cellulose, acrylates; surfactants such as polyoxyethylene (80) sorbitan monooleate and glycerin. The amount of demulcent may vary. In some embodiments, the amount of any demulcent such as those listed above may be from about 0.1% w/w to about 2% w/w, or from about 0.3% w/w to about 0.7% w/w, or from about 0.3% w/w to about 0.5% w/w, or about 0.5% w/w.

An ophthalmologically acceptable liquid may include a buffer. The buffer may vary, and may include any weak conjugate acid-base pair suitable for maintaining a desirable pH range. Examples include, but are not limited to, acetate buffers, citrate buffers, phosphate buffers, borate buffers, or a combination thereof. Acids or bases may be used to adjust the pH of these formulations as needed. The amount of buffer used may vary. In some embodiments, the buffer may have a concentration in a range of about 1 nM to about 100 mM. The pH of a buffered solution may be increased by the addition of sodium hydroxide or another base, or decreased by the addition of hydrochloric acid or another acid. In some embodiments, the pH of a composition may be from about 7 to about 8, 7.2 to about 7.8, or from about 7.4 to about 8.0.

An ophthalmologically acceptable liquid may include a preservative. The preservative may vary, and may include any compound or substance suitable for preventing microbial contamination in an ophthalmic liquid subject to multiple uses from the same container. Preservatives that may be used in the pharmaceutical compositions disclosed herein include, but are not limited to, cationic preservatives such as quaternary ammonium compounds including benzalkonium chloride, polyquad, and the like; guanidine-based preservatives including polyhexamethylene biguanide (PHMB), chlorhexidine, and the like; chlorobutanol; mercury preservatives such as thimerosal, phenylmercuric acetate and phenylmercuric nitrate; and oxidizing preservatives such as stabilized oxychloro complexes (e.g. Purite®). Purite® is a registered trademark of Allergan, Inc.

In some embodiments, the amount of preservative in the liquid may be from about 0.0001% w/w to about 25% w/w, or from about 0.002% w/w to about 0.05% w/w, or from about 0.005% w/w to about 0.02% w/w, or about 0.01% w/w.

An ophthalmologically acceptable liquid may include a surfactant. The surfactant may vary, and may include any compound that is surface active. A surfactant may be used for assisting in dissolving an excipient or an active agent, dispersing a solid or liquid in a composition, enhancing wetting, modifying drop size, stabilizing an emulsion, or a number of other purposes. Useful surfactants include, but are not limited to, surfactants of the following classes: alcohols; amine oxides; block polymers; carboxylated alcohol or alkylphenol ethoxylates; carboxylic acids/fatty acids; ethoxylated alcohols; ethoxylated alkylphenols; ethoxylated arylphenols; ethoxylated fatty acids; ethoxylated fatty esters or oils (animal and vegetable); fatty esters; fatty acid methyl ester ethoxylates; glycerol esters; glycol esters; lanolin-based derivatives; lecithin and lecithin derivatives; lignin and lignin derivatives; methyl esters; monoglycerides and derivatives; polyethylene glycols; polymeric surfactants; propoxylated and ethoxylated fatty acids, alcohols, or alkyl phenols; protein-based surfactants; sarcosine derivatives; sorbitan derivatives; sucrose and glucose esters and derivatives. In some embodiments, the surfactant may include polyethylene glycol (15)-hydroxystearate (CAS Number 70142-34-6, available as Solutol HS 15® from BASF), polyoxyethylene-polyoxypropylene block copolymer (CAS No. 9003-11-6, available as Pluronic® F-68 from BASF), polyoxyethylene 40 stearate (POE40 stearate), polysorbate 80 or polyoxyethylene (80) sorbitan monooleate (CAS No. 9005-65-6), sorbitane monostearate (CAS No. 1338-41-6, available as Span™ 60 from Croda International PLC), polyoxyethylenglyceroltriricinoleat 35 (CAS No. 61791-12-6, available as Cremophor EL® from BASF). The amount of surfactant may vary. In some embodiments, the amount of any surfactant such as those listed above may be from about 0.001% w/w to about 5% w/w, or from about 0.1% w/w to about 2 w/w %, or from about 0.3% to about 0.7%, or from about 0.3% w/w to about 0.5% w/w, or from about 0.1% w/w to about 1% w/w, or about 0.5% w/w.

Also provided is a method for preventing or treating a disease and/or disorder in the ophthalmic field, comprising administering to the eye of a subject in need thereof an ophthalmic composition according to the invention comprising an effective amount of a drug-loaded micelle. The subject is preferably a mammal, more preferably a human subject. The disease or disorder is selected from the group consisting of glaucoma, infections, inflammations, allergies, dry eye disease, age-related macular degeneration (AMD), diabetic retinopathy, diabetic macular edema, retinal vein occlusion, uveitis, post-operative macular edema and herpetic eye disease.

In one embodiment, the invention provides a method for preventing or treating glaucoma, comprising administering to the eye of a subject in need thereof an effective amount of a micelle according to the invention that is loaded with an anti-glaucoma drug, preferably selected from drugs that lower the intraocular pressure (TOP), prostaglandins, alpha-adrenergic receptor agonists, carbonic anhydrase inhibitors (CAIs), beta blockers, miotics, neuroprotective agents, and any combination thereof.

Preferably, the micellar composition is administered topically or by injection. Other preferred routes of administration include subconjunctival administration, administration trough tenon's capsule, administration via retrograde transport trough optic nerve fibers, and retrobulbar administration. The micellar delivery system can be directly injected itself or in the form of a degradable or non-degradable depot into the eye, e.g. by subretinal, intreavitreal, intracameral and/or intrauveal injection.

LEGEND TO THE FIGURES

FIG. 1. A) Chemical structure of dodecyne modified deoxyuridine, represented as U. B) Formation of lipophilic DNA nanoparticles employing hydrophobic, covalent or aptameric interactions, respectively.

FIG. 2. A) Details on lipid modified oligonucleotides used as eye drops on rat eyes. B) Fluorescence images of the adhesion of U4T-12 to the cornea at specific time points after eye drop administration. C) Fluorescence images of 12mer control sequences (single stranded (ss) and double stranded (ds)) applied as eye drops, functionalized with a green fluorescent dye (after 30 minutes).

Figure 3:
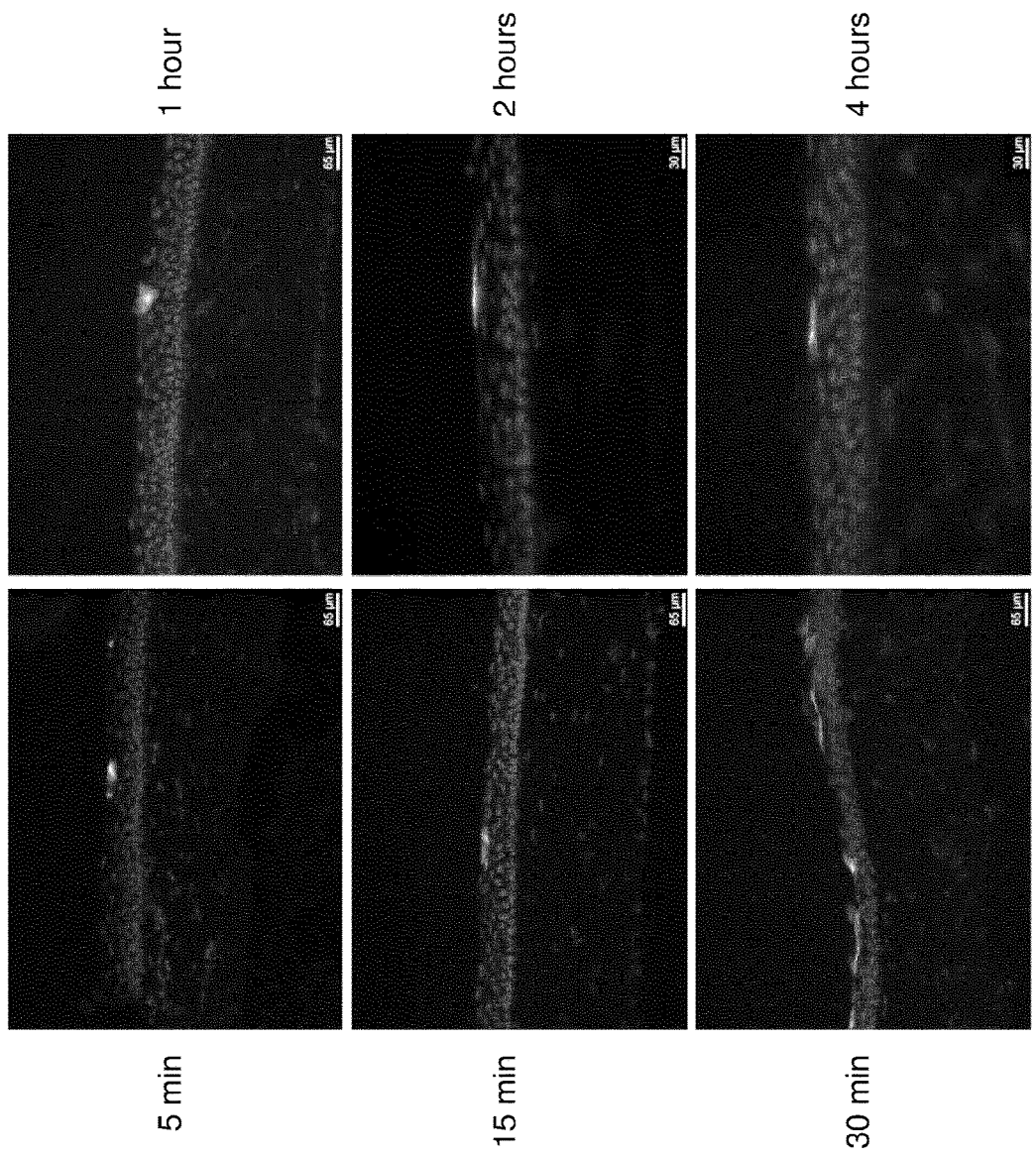

FIG. 3. Fluorescence images of time dependent adherence of U4T-12 to the cornea.

Figure 4:
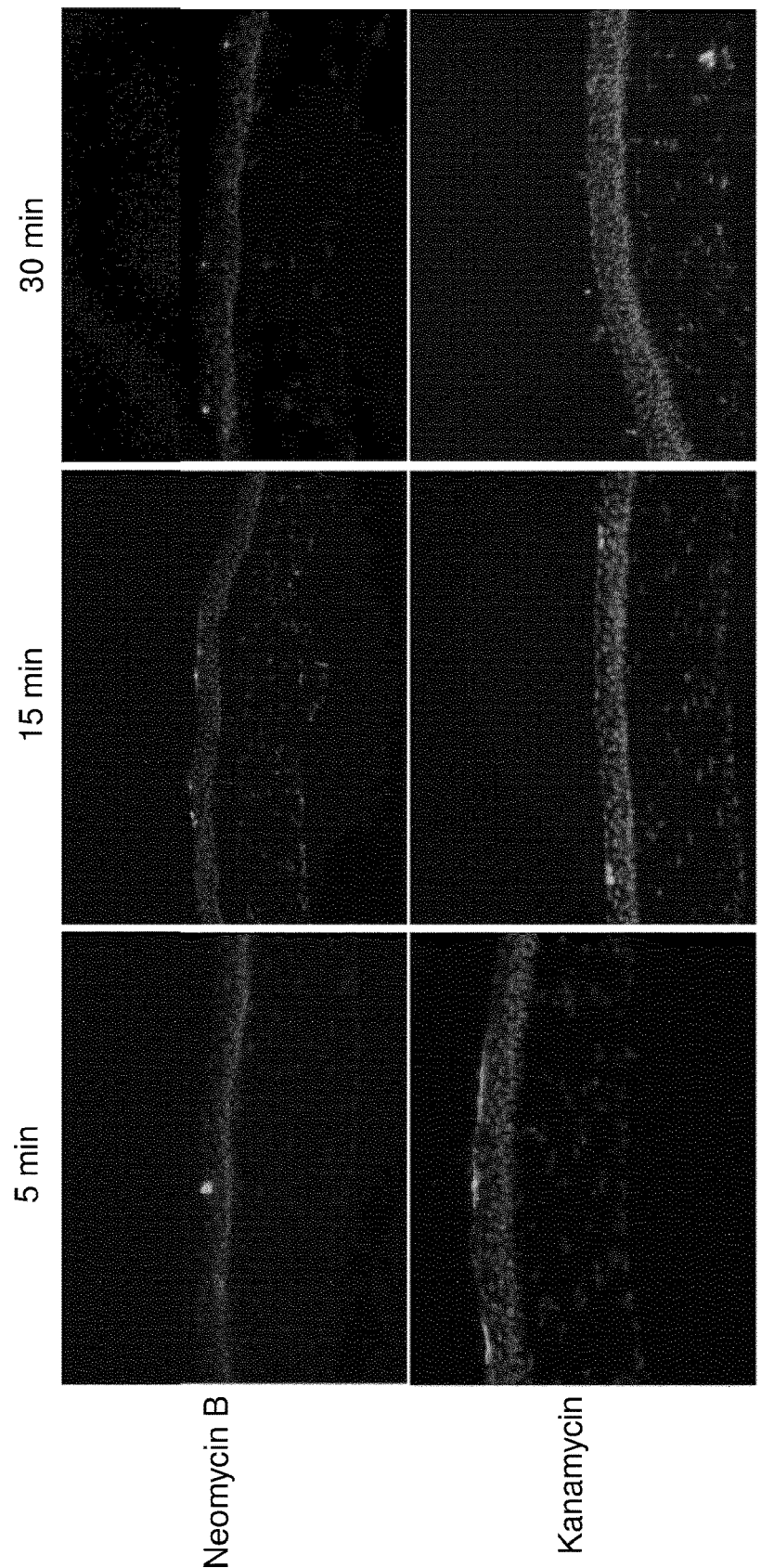

FIG. 4. Fluorescence images of adherence of neomycinB (top) and kanamycinB (bottom) loaded NPs to the cornea.

FIG. 5. *E. coli* growth dependence on antibiotic concentration a) neomycinB and b) kanamycinB, for the free compound (squares), the antibiotic loaded in the NP (circles) and the antibiotic loaded in the NP in the presence of DNA/RNAse (triangles).

Figure 6:
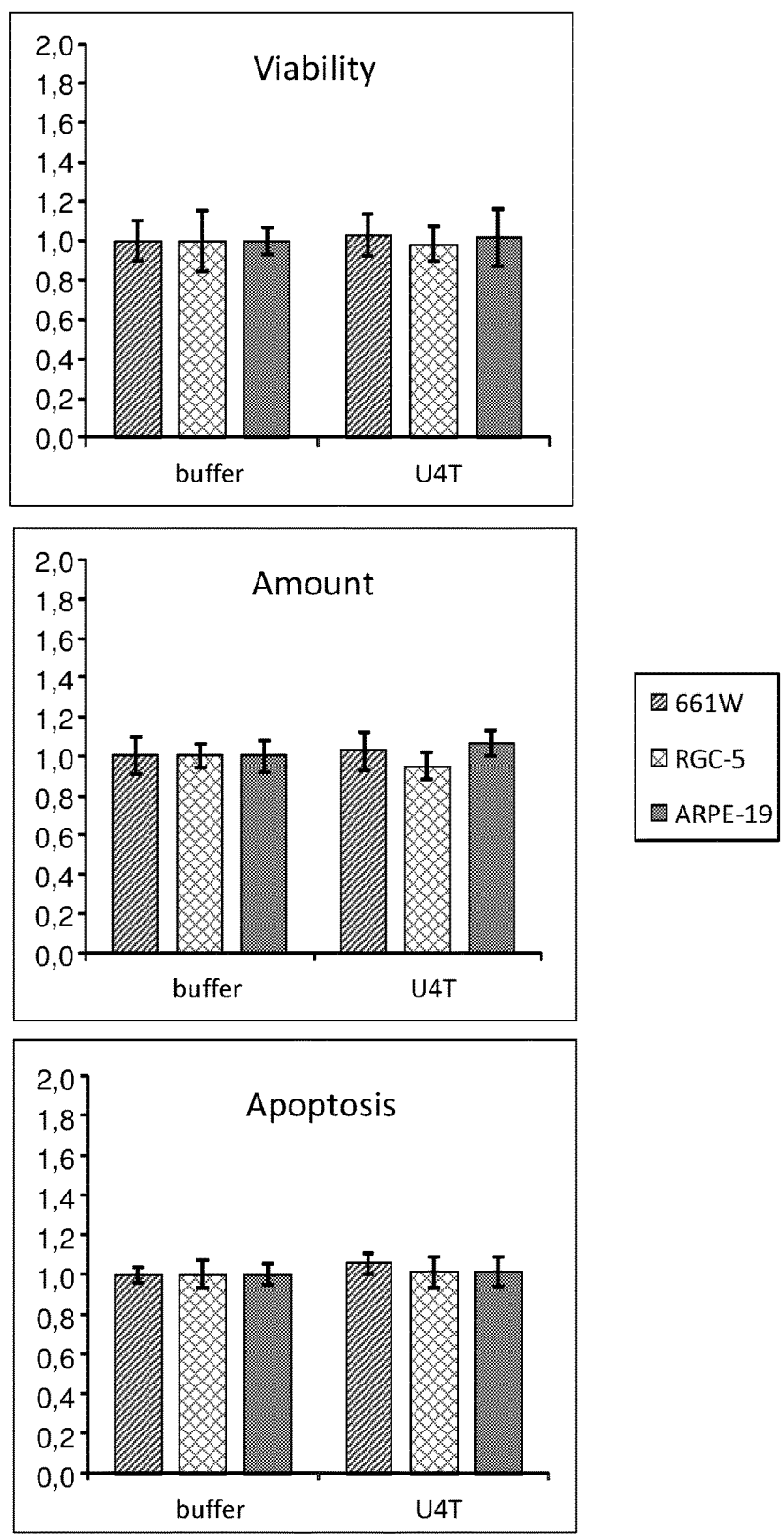

FIG. 6. Toxicity studies on U4T-12 and the buffer alone for 661W, RGC-5 and ARPE-19 cells. Cultures were screened for cell viability (left panel), cell amount (center panel) and apoptosis induction (right panel) after 24 h of incubation.

Figure 7:
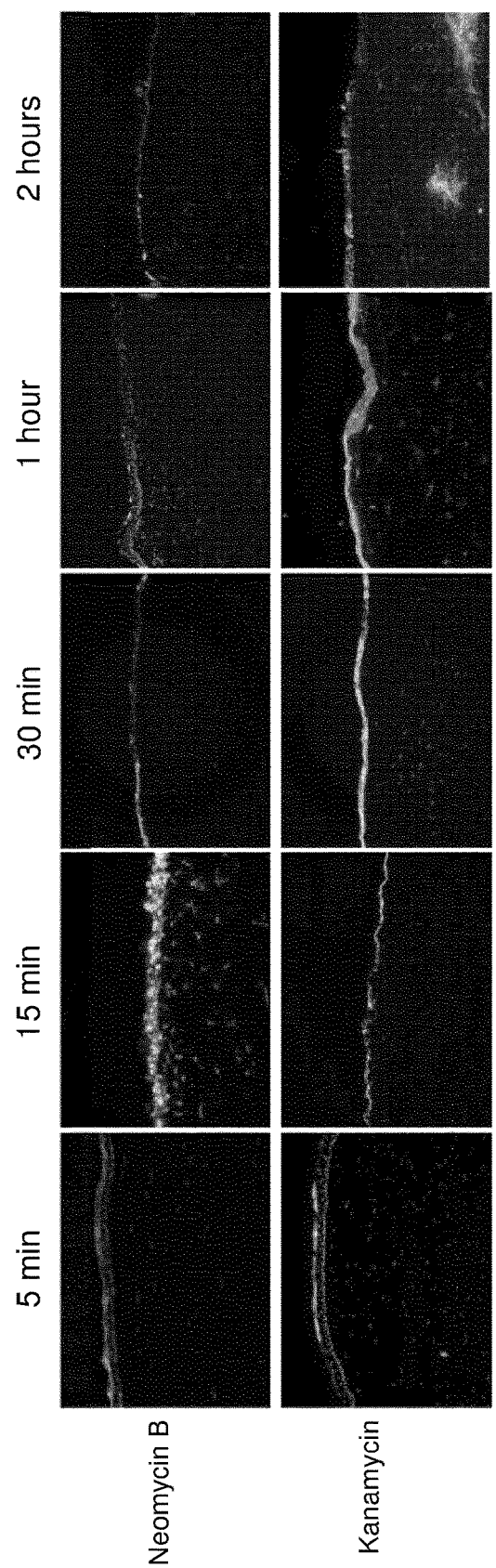

FIG. 7. Fluorescence images of adherence of neomycinB (top) and kanamycinB (bottom) loaded NPs to human cornea.

Figure 8:
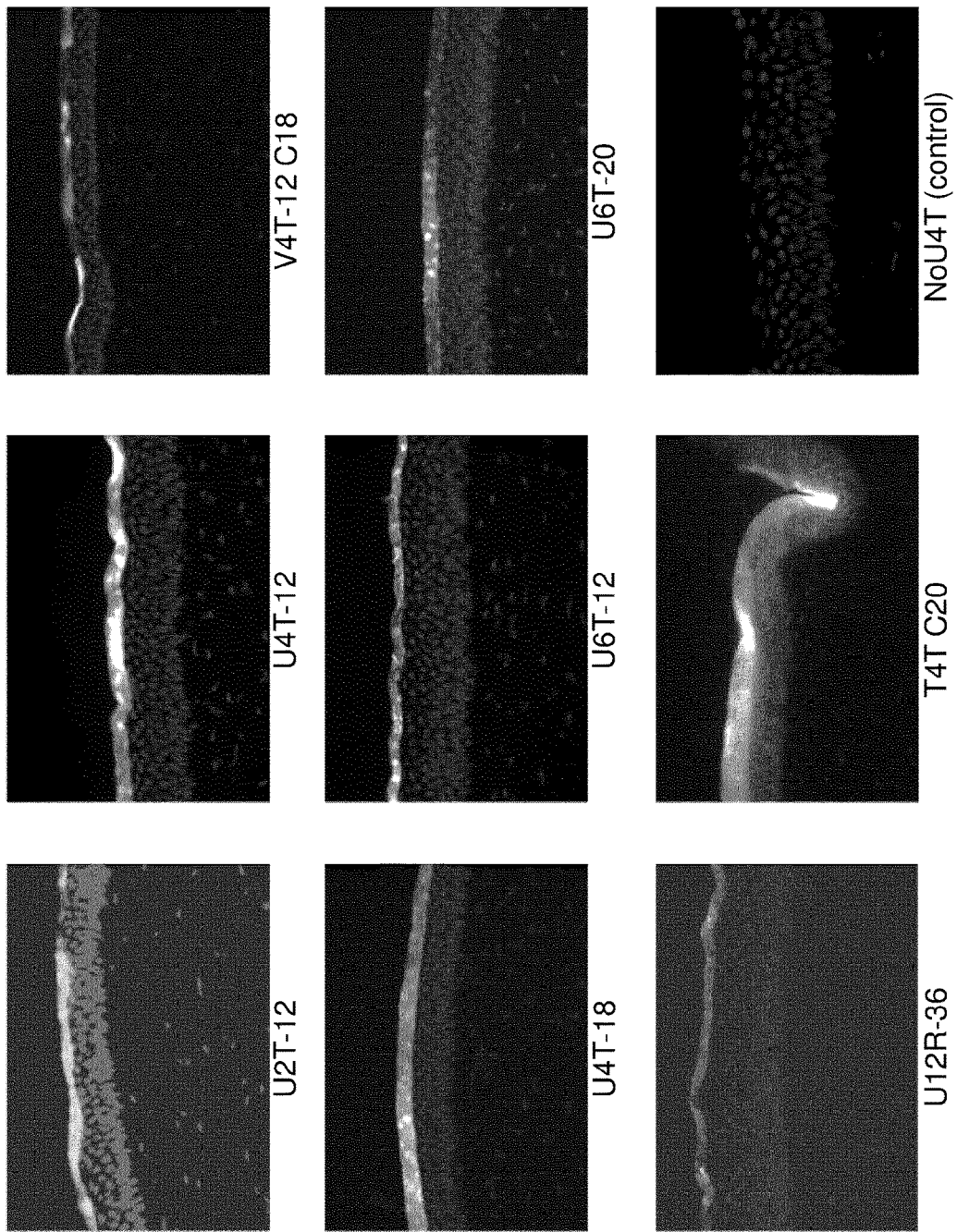

FIG. 8. Representative fluorescent images of adherence of different NPs to the porcine corneal tissue. Eyes were incubated with the NPs for 15 minutes and thoroughly washed afterwards. Cell nucleus staining was performed as described in Example 1, using DAPI.

Figure 9A:
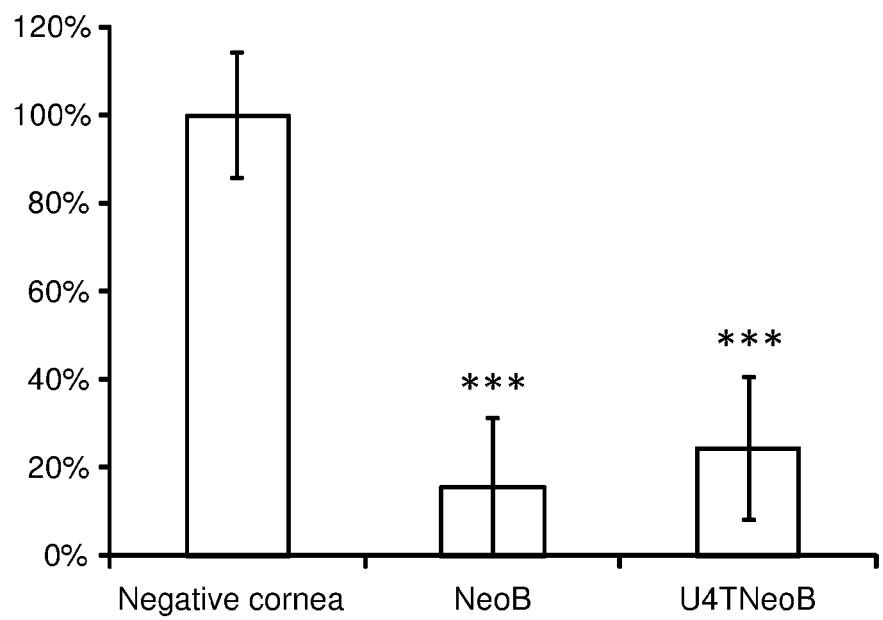
Figure 9B:
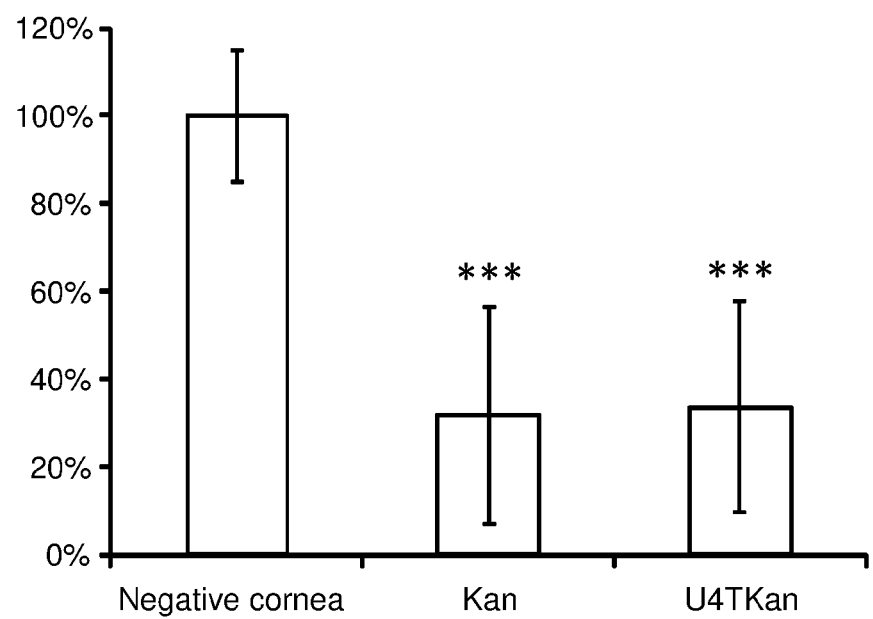

FIG. 9. Normalized bacterial growth on porcine corneas treated with control, antibiotic and antibiotic loaded NPs (U4T). Panel A: neomycin B. Panel B: kanamycin. Control (negative cornea) was set at 100%. Statistical differences are shown as *** with $p<0.001$ compared to negative cornea. Comparison between the antibiotics did not show significant differences.

Figure 10:
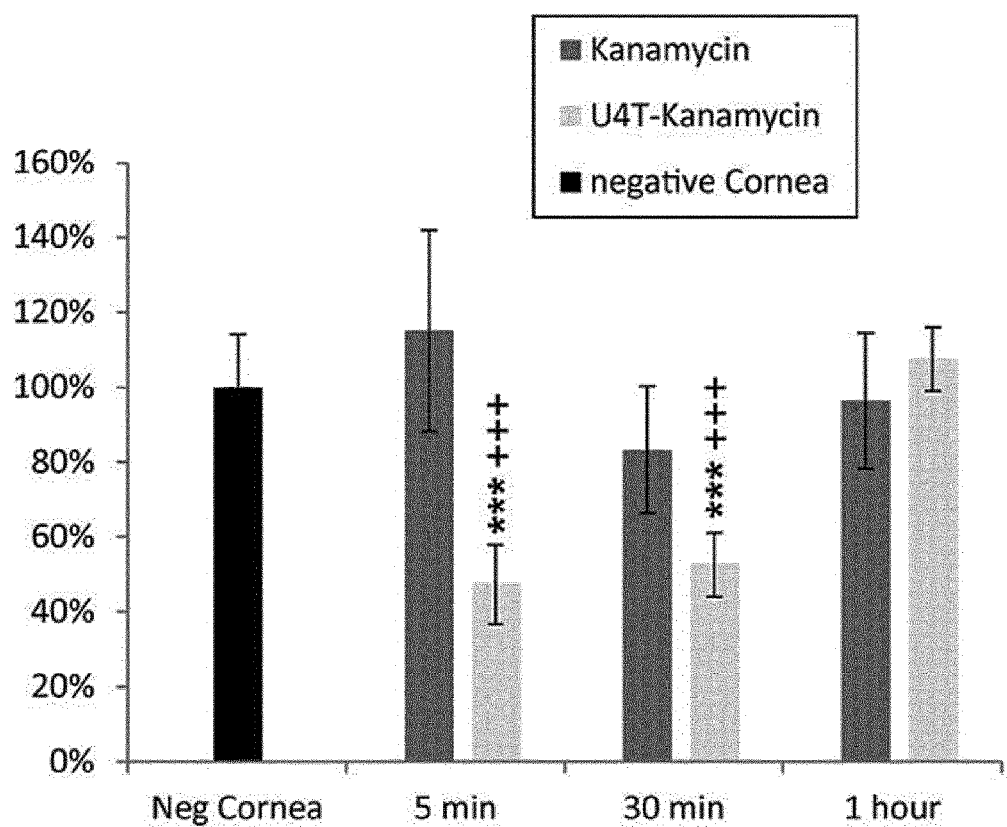

FIG. 10. Normalized bacterial growth on porcine corneas with varying washing times (5 min-1 hour). Control (negative cornea) is set to 100%. Statistical differences are shown as *** with $p<0.001$ compared to negative cornea. Comparison between Kanamycin and U4T-Kanamycin are shown as +++ with $p<0.001$. Unmarked time-points were not significantly different. Differences between the time-points were not evaluated.

EXPERIMENTAL SECTION

This section exemplifies the novel concept for a general drug delivery platform based on modularly assembled amphiphilic biopolymers, which we demonstrate through ophthalmic medication on the cornea. By incorporation of several hydrophobically-modified 2'-desoxyuridines (U) (see FIG. 1A) or other variant amphiphilic nucleotides into DNA strands amphiphiles are formed that self-assemble into micellar aggregates through microphase separation.[27] The resulting nanoparticles exhibit a corona of single stranded DNA that can be easily functionalized by hybridization. For the purpose of imaging we hybridized an oligonucleotide functionalized with a fluorophore (see FIG. 1B). For drug loading, a DNA aptamer binding kanamycinB[28] and a RNA aptamer binding neomycinB[29] were extended at the 3' position with the complementary sequence of the DNA amphiphile. Watson-Crick base pairing of aminoglycoside complexed aptamers and DNA nanoparticles resulted in two antibiotic loaded nanocarrier systems (see FIG. 1B). Previously we showed that these micelles have a small hydrodynamic diameter of approximately 7 nm, depending on the number of hydrophobically-modified nucleotides[27] and the aggregation number of similar lipid-DNA constructs was around 25.[30]

Materials and Methods

General

All chemicals and reagents were purchased from commercial suppliers and extract (BD) and tryptone (BD). All lipid modified oligonucleotides (ODNs) were synthesized using standard used without further purification, unless otherwise noted. The 1-dodecyne, eiconasol, copper(I)iodide, tetrakis(triphenylphosphine)palladium(0), neomycin trisulfate hydrate, kanamycin sulfate and diisopropylamine were purchased from Sigma-Aldrich and used as received. Other special chemicals obtained from different chemical sources were 5'-DMT-S-Iodo deoxy Uridine (Chemgenes), 1-octadecyne (GFS Chemicals), yeast automated solid-phase phosphoramidite coupling methods on an ÄKTA oligopilot plus (GE Healthcare) DNA synthesizer. All solvents and reagents for oligonucleotide synthesis were purchased from Novabiochem (Merck, UK) and SAFC (Sigma-Aldrich, Netherlands). Solid supports (Primer Support™, 200 μmol/g) from GE Healthcare were used for the synthesis of DNA. Oligonucleotides were purified by reverse-phase high pressure liquid chromatography (HPLC) using a C15 RESOURCE RPC™ 1 mL reverse phase column (GE Healthcare) through custom gradients using elution buffers (A: 100 mM triethylammonium acetate (TEAAc) and 2.5% acetonitrile, B: 100 mM TEAAc and 65% acetonitrile). Fractions were desalted using centrifugal dialysis membranes (MWCO 3000, Sartorius Stedim). Afterwards the oligonucleotides were characterized by MALDI-TOF mass spectrometry using a 3-hydroxypicolinic acid matrix. Spectra were recorded on an ABI Voyager DE-PRO MALDI TOF (delayed extraction reflector) Biospectrometry Workstation mass spectrometer. The concentrations of the DNA were measured on a SpectraMax M2 spectrophotometer (Molecular Devices, USA) using 1 cm light-path quartz cuvette. Fluorescently labeled and unmodified oligonucleotides were purchased from Biomers.net at HPLC purification grade. 1H-NMR and 31P-NMR spectra were recorded on a Varian Mercury (400 MHz) NMR spectrometer at 25° C. High-resolution mass spectra (HRMS) were recorded on an AEI MS-902 (EI+) instrument. Column chromatography was performed using silica gel 60 Å (200-400 Mesh). For minimum inhibitory concentration tests a Synergy HT multi-mode microplate reader (BioTek, Bad Friedrichshall, Germany) was used to monitor the absorption at 600 nm.

Example 1. Synthesis and Characterization of Amphiphilic Oligonucleotides

Scheme 1. Synthesis of 5-(dode-1-cynyl) uracil phosphoramidite. a:

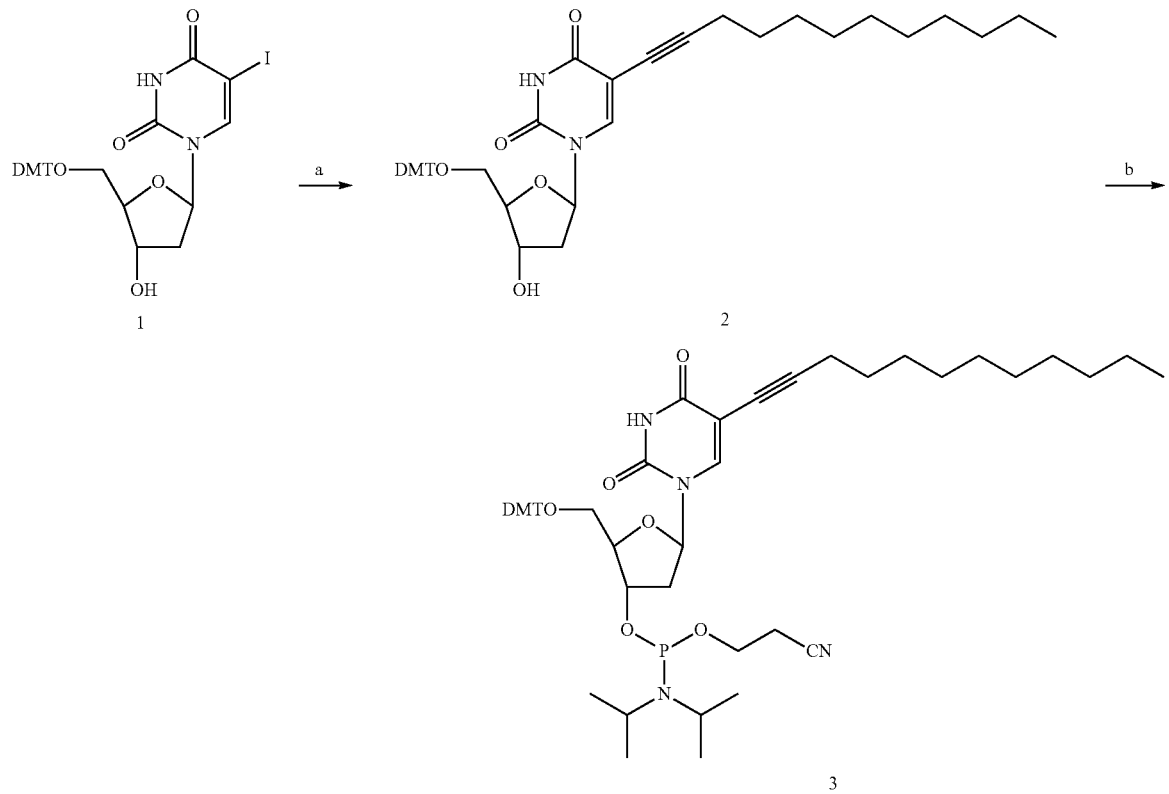

DMT: 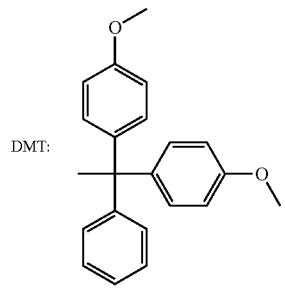

The modified 5-(dodec-1-ynyl)uracil phosphoramidite 3 (representing a hydrophobically modified nucleotide comprising a C12 alkyl hydrocarbon chain) was synthesized in two steps as previously reported in our group starting from 1 (Kwak, M. et al. Virus-like Particles Templated by DNA Micelles: A General Method for Loading Virus Nanocarriers. Journal of the American Chemical Society 132, 7834-7835 (2010)). The modified uracil phosphoramidite was dissolved in $CH_3CN$ to adjust the concentration to 0.15 M, in the presence of 3 Å molecular sieves. The prepared solution was directly connected to the DNA synthesizer. All oligonucleotides (see Table 1) were synthesized on a 10 μmol scale on an ÅKTA oligopilot plus (GE Healthcare) DNA synthesizer using standard β-cyanoethylphosphoramidite coupling chemistry. Deprotection and cleavage from the PS support was carried out by incubation in concentrated aqueous ammonium hydroxide solution for 5 h at 55° C. Following deprotection, the oligonucleotides were purified by using reverse-phase chromatography, using a C15 RESOURCE RPC™ 1 mL reverse phase column (GE Healthcare) through a custom gradients elution (A: 100 mM triethylammonium acetate (TEAAc) and 2.5% acetonitrile, B: 100 mM TEAAc and 65% acetonitrile). Fractions were desalted using centrifugal dialysis membranes (MWCO 3000, Sartorius Stedim). Oligonucleotide concentrations were determined by UV absorbance using extinction coefficients. Finally, the identity and purity of the oligonucleotides was confirmed by MALDI-TOF mass spectrometry and analytical anion exchange chromatography using a linear gradient elution, respectively.

TABLE 1

Synthesized amphiphilic oligonucleotides and found mass.

| Name | Sequence (5' → 3') | Lipid modified base (#(%)) | Calculated (m/z) | Found (m/z) |
|---|---|---|---|---|
| U2T-12 | UUTGGCGGATTC | 2(17) | 3968 | 3978 |
| U4T-12 | UUUUGCGGATTC | 4(33) | 4243 | 4242 |
| U4T-18 | UUUUGCGGATTCGTCTGC | 4(22) | 6089 | 6087 |
| U6T-12 | UUUUUUGGATTC | 6(50) | 4534 | 4507 |
| U6T-20 | UUUUUUGCGGATTCGTCTGC | 6(30) | 6998 | 6997 |

TABLE 1-continued

Synthesized amphiphilic oligonucleotides and found mass.

| Name | Sequence (5' → 3') | Lipid modified base (#(%)) | Calculated (m/z) | Found (m/z) |
|---|---|---|---|---|
| U12R-36 | (UUUUGCGGATTC)$_3$ | 12(33) | ND | ND |
| U20R-60 | (UUUUGCGGATTC)$_5$ | 20(33) | ND | ND |

1.2. Preparation of Functionalized Nanoparticles (NPs)

Micelles were prepared in low bind tubes (Eppendorf) in 1×TAE buffer (40 mM Tris-Acetate, 1 mM EDTA, 20 mM NaCl, 12 mM $MgCl_2$, pH 8.0) at a concentration of 100 μM. The lipid modified oligonucleotide of interest was prepared at the desired concentration and one equivalent of the complementary DNA was added and hybridized using a thermal gradient (90° C., 30 min; −1° C./2 min until room temperature (RT)). When nanoparticles were used for fluorescent imaging a 5' Atto488 functionalized complementary DNA was used. Afterwards the NPs were diluted 5 times in ultrapure water and used as eye drops.

Antibiotic loaded NPs were prepared at the needed concentration (20 μM) in 0.2×TAE buffer (8 mM Tris-Acetate, 0.2 mM EDTA, 4 mM NaCl, 2.4 mM $MgCl_2$, pH 8.0). For loading of neomycin B or kanamycin B, a RNA or DNA aptamer was used, respectively (Jiang, L. et al. Structure 7, 817-827 (1999); Song, K.-M. et al. Analytical Biochemistry 415, 175-181 (2011). Both aptamers were elongated with the complementary sequence of the carrier (Table 2). The lipid modified oligonucleotide and the complementary DNA-aptamer (1 eq) were loaded in a tube at the desired concentration and hybridized using a thermal gradient (80° C., 30 min; −1° C./2 min until RT). When nanoparticles were used for fluorescent imaging a 5' Cy3 functionalized complementary DNA was used, Cy3 was chosen in order not to confuse antibiotic loaded from unloaded NPs. Subsequently, for neomycinB two equivalents of antibiotic were added and for kanamycinB one equivalent (10 mM stock solution in ultrapure water). The solution was incubated at RT for a minimum of 30 minutes and used without further dilution.

TABLE 2

Used aptamers for antibiotic loading of NPs

| Name | Sequence (5' → 3') |
|---|---|
| cU4T-NeoB | ggacugggcgagaaguuuaguccgcuaauccgcaaaa |
| cU4T-KanB | TGGGGGTTGAGGCTAAGCCGATTGAATCCGCAAAA |

1.3. Minimum Inhibitory Concentration Tests

For inhibitory test *Escherichia coli* (*E. coli*), kindly donated by Sukirthini Balendran, Molecular Genetics Laboratory, Centre for Ophthalmology, Institute for Ophthalmic Research, Tubingen was grown in 1×LB medium (0.5% yeast extract, 1% tryptone, 1% NaCl) at 37° C. Obtained solution was diluted to 0.3 $OD_{600}$ units using 1×LB medium and loaded in a 96 well plate (200 µL/well). The antibiotic or antibiotic loaded NP was added and the $OD_{600}$ was monitored every 5 minutes while incubating at 37° C. When nanoparticles were used, they were prepared as described above at 800 µM. For studies including DNAse or RNAse 2 µL of 10 mg/mL RNAse or DNAse was added to each well.

1.4. Cell Culture Studies

Cell culture studies were performed as previously described in detail.[31, 32] A short description and any changes are noted below.

1.4.1 MTS Viability Assay

Twenty-four hours after supplementation, 20 µl of the CellTiter 96® AQueous One Solution Reagent (Promega) was directly added to the culture wells and incubated for 90 minutes. Then the absorbance was recorded at 490 nm with a Microplate Reader (BioTek, Synergy HT, Bad Friedrichshall, Germany) with the correction of interference at 690 nm.

1.4.2 Crystal Violet Staining

After the MTS assay, medium was removed and the cells fixed overnight with 4% paraformaldehyde. After washing the cells three times, they were stained with crystal violet solution (Sigma Aldrich, Steinheim, Germany) washed again and incubated with 1% SDS for 1 h. Absorbance was determined at 595 nm (BioTek, Synergy HT, Bad Friedrichshall, Germany).

1.4.3 Caspase 3/7 Activity Assay

Twenty-four hours after supplementation, caspase 3/7 activity was determined using CaspaseGlo 3/7 activity kit (Promega, Madison, USA) according to the manufacturer's protocol. Luminescence was measured with a luminometer (BioTek, Synergy HT, Bad Friedrichshall, Germany).

1.4.4 Statistical Analysis

Data are represented as mean+/−SD. With every assay five-six different experiments were conducted per cell line and U4T or buffer, respectively (n=5-6). Statistical analysis was performed using JMP® (version 9.0.0, SAS Institute Inc., Cary, N.C., USA). Students t-test was used for comparison between buffer vs. U4T. Differences were considered to be significant at $p<0.05$.

1.5. Animal Studies

Adult Lister Hooded Rats were obtained from Harlan Winkelmann, Germany. For the eye drop applications the conscious rats were very shortly fixated and a drop was administered to the eye using a single drop device as in medical applications. Blinking of the eyes was not hindered during drop application or afterwards. After the designated incubation time-point the rat were sacrificed with carbon dioxide inhalation.

After the predetermined time point the animal was sacrificed and the eyes were enucleated and frozen in Tissue-Tek O.C.T. (Sakura Finetek, Germany) in liquid nitrogen. Frozen sections were longitudinally cut (12 µm) on a cryostat (Leica CM 1900, Germany), thaw-mounted onto glass slides (Superfrost plus, R. Langenbrinck Labor- and Medizintechnik, Germany) and stored at −30° C. until further use. Further processing was performed using standard procedures. Briefly, for visualisation sections were fixed with methanol and to stain nuclei, sections were further incubated in a solution containing 0.2 µg/ml 4',6-diamidino-2-phenylindol (DAPI) for 1 min. Stained sections were embedded in FluorSave (Calbiochem, Germany) and imaged using a fluorescent microscope (Axioplan2 Imaging®, Zeiss, Germany with the Openlab software, Improvision, Germany).[33] Animals were treated according to the Principles of laboratory animal care (NIH publication No. 85-23, revised 1985), the OPRR Public Health Service Policy on the Human Care and Use of Laboratory Animals (revised 1986) and the German animal protection law (Research permission AK3/11 to S.S.)

1.6. Human Cornea Experiments

Five human cornea rims kindly provided by the Cornea Bank of the University Eye Hospital Tubingen were used for these studies. These rims are leftover tissue after a corneal transplantation. After the transplantation the cornea rims were returned to the cornea media (KM1, Biochrom, Deutschland) until further use. Before applying the nanoparticles the corneas were cut into 3-4 equal sized pieces, transferred to a 24-well plate and washed with PBS (PAA, Germany). Afterwards, 100 µl of the nanoparticles were applied on top of the cornea and incubated at room temperature for the designated time. Then the corneas were transferred to another well containing 2 ml of PBS and washed for the designated time at room temperature. Next the corneas were frozen in Tissue Tek, cut on a cryostat, stained with DAPI and photographed as described previously.

1.7 Results

Micellar systems are highly dynamic. Therefore, the inventors hypothesized that they can interact with the outermost hydrophobic layer of the cornea. To confirm this hypothesis and to get more insights about the structural requirements for adhesion, several DNA lipid nanoparticles were exposed to corneal epithelium of living rats. The particles were composed of different DNA-based amphiphiles: U2T-12, U4T-12, U4T-18, U6T-12, U6T-20, U12R-36 and U20R-60 (see FIG. 2A). In these abbreviations the first characters determine the number of hydrophobically modified U nucleotides present and their corresponding position (T for 5' terminal and R for a U4T-12 strand being regularly hybridized on a template), whereas the number after the hyphen describes the total number of nucleotides of the double strand. For example, U2T-12 contains 2 U's at the 5' terminus and in total is composed of 12 nucleotides. It must be mentioned that U12R-36 and U20R-60 consist of three and five repeats of U4T-12, respectively, and were fabricated by hybridization of single stranded U4T-12 with the corresponding template coding for the repeated sequence. The exact composition of all structures is given in FIG. 2A.

The eye drops containing the different fluorescently labelled DNA amphiphiles at a concentration of 20 µM were administered to conscious rats using a single drop of 30 µL and 30 min, 2 or 24 h after application the animals were sacrificed. Cryo sections of the treated eyes were prepared and imaged using fluorescence microscopy. As controls, single stranded (ss) and double stranded (ds) DNA lacking the lipid-modified nucleotide were administered as eye drops in the same fashion. Selection of the best carrier was performed by comparing the number of DNA amphiphile stained eyes to the total number of eyes to which eye drops were given and, in the case of an equal amount of positives, by visual comparison of the cryo sections (see Table 3).

TABLE 3

Number of NP positive eyes out of total number eyes.

| Time | U2T-12 | U4T-12 | U4T-18 | U6T-12 | U6T-20 | U12R-36 | U20R-60 |
|---|---|---|---|---|---|---|---|
| 30 min | 2/4 | 6/6 | 4/5 | 3/3 | 2/2 | 2/2 | 0/2 |
| 2 hours | 0/4 | 4/6 | 0/4 | 1/4 | 1/3 | 1/2 | 0/2 |
| 24 hours | 0/4 | 0/4 | 0/4 | 0/1 | 0/3 | 0/2 | 0/2 |

Among the tested amphiphiles, U4T-12 shows best attachment to the corneal epithelium (see FIG. 2B) while both ss and ds 12mer control sequences without any lipid modification do not show any affinity at all (see FIG. 2C). When comparing the content of U within the sequence, around 30% generates most efficient adhesion and ds oligonucleotides with lower (U2T-12) or higher percentage of U (U6T-12) adhere significantly less. When comparing amphiphiles with a similar ratio of U present in the sequence (U4T-12, U6T-20, U12R-36 and U20R-60), strands with increasing number of nucleotides show less adherence. Therefore, both the number of lipid modified nucleotides and the total length of the nucleotide are important parameters determining adhesion to the cornea.

In addition, it was found that incorporation of consecutive hydrophobically modified nucleotides inside the nucleic acid rather than at its 5' or 3' end, did not yield nanoparticles showing good corneal adherence. For example, amphiphile U2M-12 was prepared having the sequence TCCUUG-GCGCAG. Micelles composed of U2M-12 showed hardly any adherence to the porcine cornea (data not shown). This is in contrast to U2T-12, which contains the same number of lipid modified nucleotides (see above) but with the modified nucleotides situated at the end of the chain, while for U2M-12 they are situated inside the chain. This indicates that positioning of the lipid modified nucleotides at the terminal end of the nucleic acid is important for obtaining micelles showing affinity to the cornea.

After selection of U4T-12 as the best carrier, the adherence time on the cornea was evaluated (see FIG. 3). The NPs of U4T-12 are already observed 5 min after application of the eye drops, thus showing a fast adherence to the cornea. Then the NPs are present for a period of at least four hours because distinct green fluorescence of the carrier was clearly visible. This adherence time is significantly longer than currently applied ocular medication and thus makes our DNA NPs a promising vehicle for ocular drug delivery. After these successful proof-of-concept experiments we applied U4T-12 aptamer-functionalized carriers loaded with neomycinB or kanamycinB because these two antibiotics are currently used for treatment of ophthalmic indications. For localization of the drug loaded carrier the aptamer was functionalized with a red fluorescent dye at the 5' end. The eye drops were administered as described earlier and the adherence to the cornea was studied 5, 15 and 30 minutes after application (see FIG. 4).

Both drug loaded NPs are effectively attached to the cornea for a period of at least 30 min. These experiments indicate that adhesion to the cornea is mainly determined by the carrier system, which allows the loading of different cargoes and their close contact to the corneal surface. Important to mention in this context is that the chemical structure of the drugs was not modified due to the loading mediated by non-covalent interactions. Since DNA and RNA aptamers are known to bind a large variety of molecular structures[28, 29] these vehicles most probably represent a general delivery platform for diseases of the anterior section of the eye.

For successful application two critical issues still need to be addressed, i.e., the activity and release of the antibiotic as well as the biocompatibility of the NP. The former one was tackled by performing a minimum inhibitory concentration test (MIC-test) using Escherichia coli (E. coli)(see FIG. 5). For this purpose the action of antibiotic loaded NPs was compared to the free drugs. For these experiments RNAse and DNAse were added to the cell suspension containing neomycinB and kanamycinB loaded NPs, respectively, to mimic nuclease containing body fluids on the ocular surface.

Figure 5A:
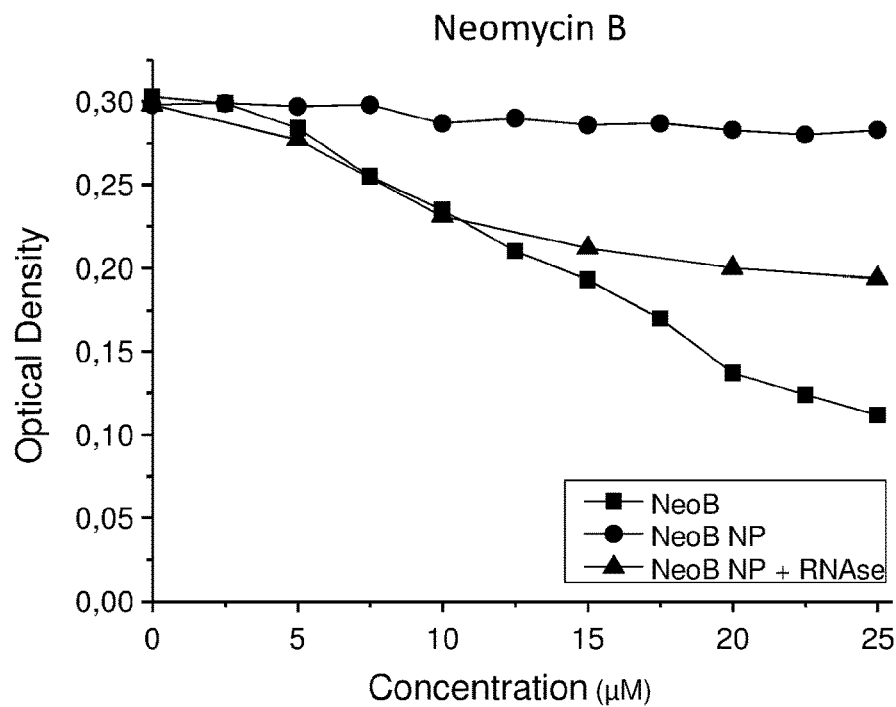
Figure 5B:
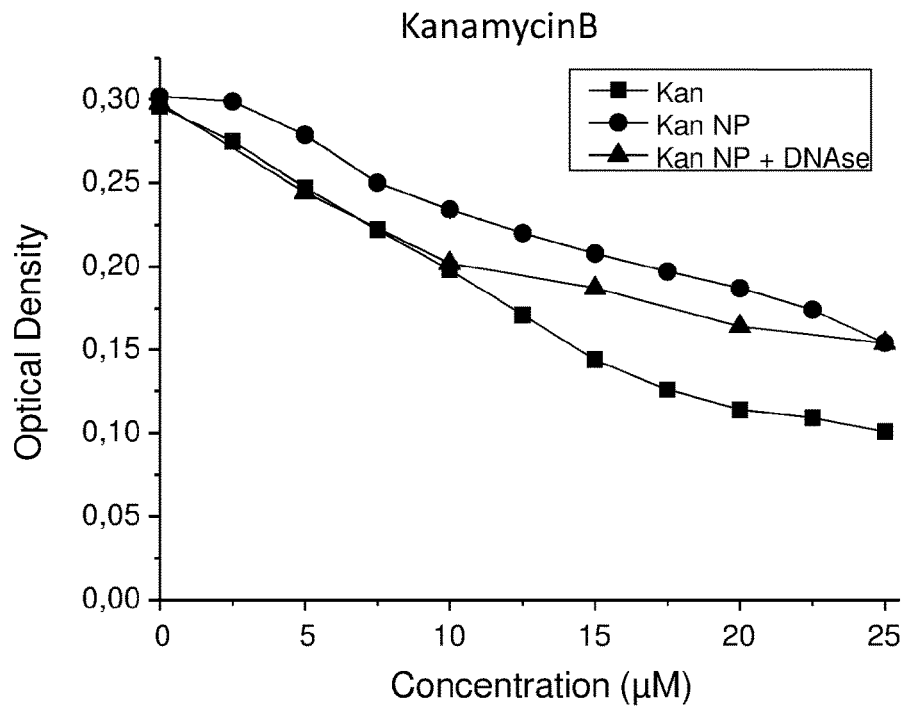

As expected, for the free aminoglycosides a clear decrease in cell growth was observed with increasing antibiotic concentration (see FIGS. 5a and 5b). In contrast, the function of neomycinB was strongly inhibited when complexed with the NP, however, in presence of RNAse the activity was recovered. In the case of kanamycinB the inhibiting effect of the aptamer is less pronounced than for neomycinB indicating that absence of DNAse also results in antibiotic activity. This is an important feature of the kanamycinB carrier since DNAses are less prevalent than RNAses.[34] In the next step the cytotoxicity of the NPs was evaluated using three different ocular cell lines. Thereby, three critical parameters were taken into account, i.e., cell amount, cell viability and apoptosis induction (see FIG. 6). The selected cell lines were 661W, RGC-5 and ARPE-19 cells, originating from human or rodent eyes, respectively.

For none of the measured parameters there was a significant difference between the NPs and the buffer after 24 h of incubation, indicating that the NPs do not show any toxic effect in this period of time. Finally, to show the high application potential of this nanosystem adherence to human corneal tissue of antibiotic loaded particles was tested. The experiments were performed on unused transplant tissue that was not needed for patients. To this extent, the tissue was incubated for five minutes in nanoparticle solution identical to the one used as eye drops and afterwards the cornea was washed. Washing times after incubation were varied from five minute to two hours (see FIG. 7).

Both neomycinB and kanamycinB loaded NPs showed a remarkable attachment to the human cornea. In addition, a marked slow decrease in intensity was observed for particles containing neomycinB with increasing washing time. This can be due to detachment of the NPs from the corneal surface or because of degradation of the aptamer. In contrast, for kanamycinB this effect was not notable, hence it is likely that the RNA aptamer used for binding of neomycin is degraded by RNAse present on the eye.

Treatment of eye diseases is accompanied with many problems. Therefore, improvement in efficacy of eye drops has been an important goal for many years. Here we have shown a novel approach for treating eye infections but the delivery concept can be generalized very easily to other indications. Our NPs exhibit no toxicity as they are composed to a great extent of natural building blocks. Moreover, they induce a dramatically increased adherence time of drugs in living animals compared to pristine eye drop-based dosage forms. Even more important, they have been proven to be applicable to human corneal tissue. The design of the carrier allows for easy functionalization with therapeutically active agents, imaging units or targeting moieties or a combination of them by simple mixing of components and hybridization to generate multifunctional NPs. A paramount feature of the drug loading is the use of aptamers that enables specific drug binding to the carrier without chemical modification or alteration of the pharmaceutical function. These findings open a variety of possibilities for employment of these materials as drug delivery vehicle for treatment of eye diseases.

Example 2. Further Amphiphilic Oligonucleotides

This example exemplifies further amphiphilic oligonucleotides, and the advantageous use thereof in a nanoparticle for ocular delivery. The first variant (V4T-12 C18) contains a nucleotide modified at the nucleobase with a C18 alkyl chain at the nucleobase. The second variant (T4T-12 C20) is a nucleic acid that is modified at the 5' OH with a C20 alkyl chain.

Scheme 2. Synthesis of 5-(octadec-1-ynyl)uracil phosphoramidite 5.

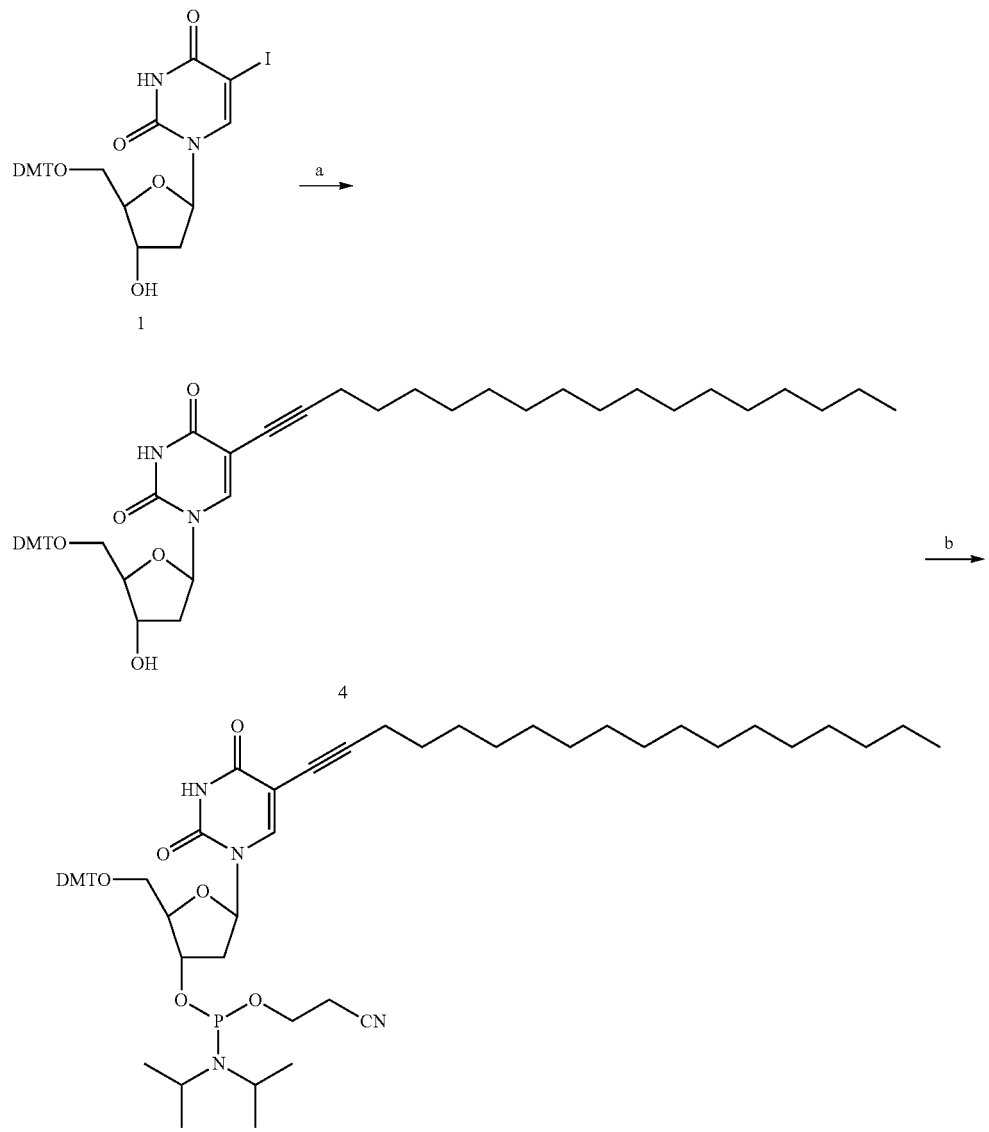

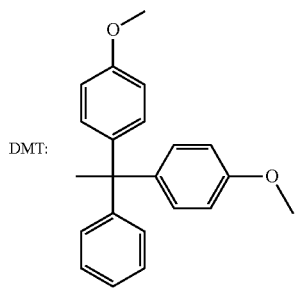

DMT:

2.1 Synthesis of V4T-12 C18

The modified 5-(octadec-1-ynyl)uracil phosphoramidite 5 (representing a hydrophobically modified nucleotide comprising a C18 alkyl hydrocarbon chain) was synthesized in two steps as described in example 1, starting from 1 (Scheme 2) (Kwak, M. et al. Journal of the American Chemical Society 132, 7834-7835 (2010)). The modified uracil phosphoramidite was dissolved in $CH_3CN$ to adjust the concentration to 0.15 M in the presence of 3 Å molecular sieves. This solution was directly connected to the DNA synthesizer. The V4T-12 C18 oligonucleotide (Table 4) was synthesized on a 10 μmol scale on an ÅKTA oligopilot plus (GE Healthcare) DNA synthesizer using standard β-cyanoethylphosphoramidite coupling chemistry.

2.2 Synthesis of T4T-12 C20

Unreacted amidite and activator were removed by filtration and the oligonucleotide was oxidized manually by exposure to $I_2$ (50 mM in a pyridine/water mixture (90/10)) for 5 minutes. The solid support was thoroughly washed with acetonitrile before further processing.

Following synthesis, deprotection and cleavage from the PS support was carried out by incubation in concentrated aqueous ammonium hydroxide solution for 5 h at 55° C. In the next step, the oligonucleotide was purified by using reverse-phase chromatography, using a C15 RESOURCE RPC™ 1 mL reverse phase column (GE Healthcare) through custom gradient elution (A: 100 mM triethylammonium acetate (TEAAc) and 2.5% acetonitrile, B: 100 mM TEAAc and 65% acetonitrile or 90% 2-propanol). Fractions were desalted using centrifugal dialysis membranes (MWCO 3000, Sartorius Stedim) or HiTrap desalting columns (GE Healthcare) V4T-12 C182.2

Scheme 3. Chemical structure and sequence of T4T-12 C20

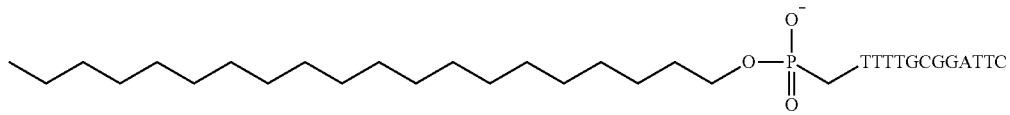

For the preparation of T4T-12 C20 eicosanol was activated as β-cyanoethylphosphoramidite. Therefore, eicosanol (0.46 g) was dissolved in a mixture of dry chloroform (10 ml) and dry dichloromethane (5 ml) under inert conditions. To this solution 1.5 equivalents of freshly distilled diisopropylethylamine and 1.5 equivalents of 2-cyanoethyl N,N-diisopropylchlorophosphoramidite were added drop wise. The solution was allowed to stir for 2 hours. Afterwards the solution was poured into chloroform (30 ml), washed with 1 M $NH_4Cl$ (15 ml) and dried over $MgSO_4$. Solvents were removed under vacuum and the product was redissolved in anhydrous chloroform to a final concentration of 0.15 M and characterized by NMR (P31 NMR, 400 MHz: 147.8 ppm)

Coupling of the eicosane modification was performed in a round bottom flask under inert conditions. First, the T4T oligonucleotide was synthesized on a 50 μmol scale on an ÅKTA oligopilot plus (GE Healthcare) DNA synthesizer using standard β-cyanoethylphosphoramidite coupling chemistry. Afterwards, the polystyrene support containing the immobilized oligonucleotide was dried and 125 mg was transferred to the round bottom flask. The reaction vessel was purged with argon for 5 minutes and 2.5 ml activator solution (0.25 M ethylthiotetrazole in anhydrous acetonitrile) was added. Subsequently, the eicosane amidite was added (1.8 ml) and the mixture was left to stir overnight.

2.3 In-Vitro Adhesion to Porcine Eye

In order to further gauge the adherence of different nanoparticles (NPs) to the eye surface, porcine eyes were obtained from the local slaughterhouse and exposed to the different NPs. The NPs were prepared as described in example 1, section 1.2, at a concentration of 20 μM. The porcine eye was transferred to a 6-well plate and 2 rings of different diameter were placed on top of the cornea to prevent spillage of the NP solution. Subsequently, 50 μl of NP solution was put on top of the cornea and incubated for 15 minutes. Afterwards, the rings were removed using tweezers and the eyes were thoroughly washed in PBS (PAA, Germany). The eye was divided into two along the visual axis. Of the two halves one was stored in formaldehyde, whereas the other was frozen in Tissue Tek, cut on a cryostat, stained with DAPI and photographed as described in example 1.

2.4 Evaluation of Antibiotic Activity on Porcine Cornea

To evaluate the antibiotic activity and time needed to wash out all NP bound antibiotics *E. coli* growth experiments were performed on corneas. To this extent, the corneas were first taken out from porcine eyes that were obtained from the local slaughterhouse and placed in a petridish. Kanamycin loaded NPs were prepared at a concentration of 100 µM as described in example 1. A rubber ring was placed around them to prevent spillage of the NP solution and 100 µl of NP solution was placed on top of the cornea ensuring the whole cornea was wetted by the solution. After 5 minutes incubation time the rings were removed. Subsequently, the corneas were shortly dried on a tissue paper or washed in excess PBS for the designated time. Afterwards the samples were placed on petrifilms (3M) prepared as recommended by the manufacturer. On top of the corneas 50 E. coli bacteria in 5 µl 1×LB medium were placed. The petrifilms were closed and incubated at 37° C. for 48 hours after which pictures of all films were taken. The number of colonies was determined in duplicate by three persons with the pictures being blinded.

Statistical Analysis

Data are represented as mean+/−SD. Statistical analysis was performed using JMP® (version 10.0.0, SAS Institute Inc.). ANOVA analysis with Tukey-Kramer post-hoc test was used for statistical evaluation of the individual timepoints and the negative cornea samples. Differences were considered to be significant at $p<0.05$.

2.5 Results

The adherence of the NPs composed of DNA amphiphiles can depend on various structural parameters. Therefore, different structure changes were introduced into the U4T-12 system, which showed the best binding to corneal tissue. First, the length of the hydrophobic alkyl chain attached to the T base was increased. To this end, 5-(octadec-1-ynyl) uracil was synthesized and used as modified nucleotide for the synthesis of V4T-12 C18. In contrast to the modified uracil of Example 1 herein above, this nucleotide is modified with an 18 carbon long chain and thus yields DNA amphiphiles with a more hydrophobic character.

Additionally, the binding of micelles formed by oligonucleotides modified at the 5' hydroxyl group and not at the nucleobase was investigated. Therefore, NPs were synthesized comprising a DNA-based amphiphile that has the same nucleic acid sequence as U4T-12 but carries an eicosane alkyl group at the 5' terminus (T4T-12 C20).

To determine the binding capabilities of the NPs, they were exposed to porcine eyes obtained from the local slaughterhouse. For comparison the NPs from example 1 were included in the experiments. After 15 minutes of incubation with the NPs, the porcine eye was thoroughly washed in PBS buffer and frozen in tissue tek. The adhesion to the cornea was evaluated by fluorescence microscopy (See FIG. 8).

For all the tested NPs good adherence to the porcine cornea is observed, while the unmodified control sequence shows no affinity. When comparing U4T-12 with V4T-12 C18 it is apparent that both NPs show good adherence. This could indicate that the length of the alkyl chain has a minor influence on binding to corneal tissue. The T4T-12 C20 NPs also show good adhesion to the corneal epithelium like the other NPs. Hence, these experiments indicate that terminal modification of the oligonucleotide with a hydrocarbon chain is a good alternative for NPs that are composed of DNA that has a lipid modification at the nucleobase.

On the other hand, terminal modification with a polypropylene polymer did not yield micelles showing adequate corneal adherence. For example, micelles comprising DNA-b-PPO diblock copolymers 22PPO(1k) prepared according to WO2009/021728 were evaluated for in-vivo rat eye adhesion. It was found that these NPs do not adhere to the cornea (data not shown). Reasons for the poor affinity can be various. PPO(1k) corresponds to approximately 16-17 repeating units, which is approximately 50 atoms long. When comparing the structure of 22PPO(1k) to that of T4T-12 C20, one can observe that the modification in 22PPO(1k) is much longer. On the other hand, it has a less hydrophobic character then the eicosane modification because it contains oxygen atoms in the backbone.

The results from Example 1 and the affinity experiments on porcine corneas demonstrate excellent adherence of the nanoparticles (NPs). In addition, it was shown that the antibiotic activity in cell medium is retained. However, a clear therapeutic effect at the site of action, the cornea, was not yet proven. To this end, growth studies of *Escherichia coli* (*E. coli*) were performed on porcine corneas where the efficiency of antibiotic loaded NPs was compared to that of the free drugs. As a positive control experiment, the antibiotic activity was first evaluated without washing. Therefore, the cornea was taken from porcine eyes and placed on a petridish. U4T-12 NPs loaded with the antibiotic neomycin or kanamycin were applied and incubated for 5 minutes. Afterwards excess of solution was removed with a tissue and the corneas were placed on petrifilms containing growth medium for *E. coli*. A total of 50 *E. coli* bacteria were applied to the cornea and allowed to grow for 48 hours after which the number of bacterial colonies was determined (See FIG. 9).

The *E. coli* growth experiments clearly show the activity of the free antibiotic. Additionally, the antibiotic bound to the NPs shows comparable bacterial growth inhibition indicating that the aptamers are successfully degraded by nucleases or release the drug payload such that neomycin B and kanamycin are liberated.

Still further growth experiments were performed using kanamycin loaded nanoparticles under conditions wherein tearing was simulated. Therefore, the same setup was utilized, but after incubation with the NPs the porcine cornea was washed in a large excess of PBS buffer for 5, 30 and 60 minutes (See FIG. 10).

The results of the *E. coli* growth experiment with different washing times highlight one of the shortcomings of current ophthalmic medication. As is visible in FIG. 10, no significant growth inhibition is observed for the free antibiotic already after 5 minutes of washing. This is in good agreement with the results of the control experiments in Example 1, where the free antibiotics were not detected by fluorescence microscopy 5 minutes after application to the living animal. When comparing the free antibiotics to the antibiotic loaded NPs one can observe that our NPs are still active even after 30 minutes of washing, but that after 1 hour of washing no significant effect is seen anymore. Again, this is in very good agreement with the adhesion time observed in the rats.

It can be therefore be concluded that the residence time of the antibiotic on the cornea is approximately 10 times longer when the NPs are used as delivery vehicle. These experiments show the superior efficacy of the antibiotic loaded NPs of the invention compared to antibiotics that are currently used for treatment.

Example 3. Exemplary Ophthalmic Formulations

Eye drop composition consisting of a buffered solution containing 40 mM Tris-Acetate, 1 mM EDTA, 20 mM NaCl and 12 mM $MgCl_2$ with a final pH of 7.4-8.0 and a micelle concentration ranging from 20 µM to 20 mM (0.03-31%) with 1-2 equivalents (eq) of drug bound.

The above buffered solution can be replaced with any of the following suitable buffer solutions:
- 20 mM NaCl and 12 mM $MgCl_2$ with a final pH of 7.4-8.0
- 40 mM Tris-Acetate, 20 mM NaCl and 12 mM $MgCl_2$ with a final pH of 7.4-8.0
- 40 mM $KH_2PO_4/K_2HPO_4$, 20 mM NaCl and 12 mM $MgCl_2$
- 45 mM Tris-borate, 20 mM NaCl and 12 mM $MgCl_2$

REFERENCES

1. Budenz, D. L. Ophthalmology 116, S43-47 (2009).
2. Tsai, J. C. Curr Opin Ophthalmol 17, 190-195 (2006).
3. Baudouin, C. et al. Progress in retinal and eye research 29, 312-334 (2010).
4. Lai Becker, M. et al., Pediatrics 123, e305-311 (2009).
5. Hermann, M. M. et al, J Glaucoma 20, 502-508 (2011).
6. Chen, J. & Seeman, N.C. Nature 350, 631-633 (1991).
7. Rothemund, P. W. K. Nature 440, 297-302 (2006).
8. Andersen, E. S. et al. Nature 459, 73-U75 (2009).
9. Mitchell, J. C. et al., Journal of the American Chemical Society 126, 16342-16343 (2004).
10. McLaughlin, C. K. et al., Chemical Society Reviews 40, 5647-5656 (2011).
11. Kwak, M. & Herrmann, A. Chemical Society Reviews 40, 5745 (2011).
12. Giljohann, D. A. et al. Angewandte Chemie International Edition 49, 3280-3294 (2010).
13. Liu, H. & Liu, D. Chemical Communications, 2625 (2009).
14. Ke, Y. et al., Science 319, 180-183 (2008).
15. Lu, C.-H. et al., Journal of the American Chemical Society 134, 10651-10658 (2012).
16. Boersma, A. J. et al., Chemical Society Reviews 39, 2083-2092 (2010).
17. Boersma, A. J. et al., Chemical Communications 48, 2394-2396 (2012).
18. Kleiner, R. E. et al. Chemical Society Reviews 40, 5707-5717 (2011).
19. Lee, H. et al. Nature Nanotechnology 7, 389-393 (2012).
20. Walsh, A. S. et al., ACS Nano 5, 5427-5432 (2011).
21. Keum, J.-W. et al., Small 7, 3529-3535 (2011).
22. Zheng, D. et al. Proceedings of the National Academy of Sciences 109, 11975-11980 (2012).
23. Rosi, N. L. Science 312, 1027-1030 (2006).
24. Jiang, Q. et al. Journal of the American Chemical Society 134, 13396-13403 (2012).
25. Ko, S. H. et al., Biomacromolecules 9, 3039-3043 (2008).
26. Alemdaroglu, F. E. et al., Advanced Materials 20, 899-902 (2008).
27. Anaya, D.-M. et al., Chemistry A European Journal 16, 12852-12859 (2010).
28. Gold, L. et al., Annual Review of Biochemistry 64, 763-797 (1995).
29. Stoltenburg, R. et al., Biomolecular Engineering 24, 381-403 (2007).
30. Kwak, M. et al. Journal of the American Chemical Society 132, 7834-7835 (2010).
31. Schnichels, S. et al. Neurochemistry International 60, 581-591 (2012).
32. Schultheiss, M. et al. Graefes Archive for Clinical and Experimental Ophthalmology 250, 1221-1229 (2012).
33. Schultheiss, M. et al. Graefes Arch Clin Exp Ophthalmol (2013)
34. Yusifov, T. N. et al. Mol Vis 14, 180-188 (2008).

The invention claimed is:

1. A method for treating an ophthalmic disease and/or disorder, comprising administering to the eye of a subject in need thereof an effective amount of a drug-loaded micelle comprising self-assembled amphiphilic biopolymers, wherein said amphiphilic biopolymer is a nucleic acid molecule comprising at the 3' or 5' end a stretch of at least 2 contiguous hydrophobically-modified 2'-deoxyuridine nucleotides with a hydrophobic moiety, wherein the hydrophobic moiety is a hydrocarbon chain of 6 to 30 C-atoms, the content of modified 2'-deoxyuridine within the nucleic acid molecule is about 30% or higher, and the nucleic acid molecule has at least 10 and less than 60 nucleotides.

2. The method according to claim 1, wherein the disease and/or disorder is selected from the group consisting of glaucoma, infections, inflammations, allergies, dry eye disease, age-related macular degeneration (AMD), Diabetic retinopathy, diabetic macular edema, retinal vein occlusion, uveitis, post operative macular edema and herpetic eye disease.

3. The method according to claim 2, wherein the micelle is loaded with an anti-glaucoma drug.

4. A method for treating an ophthalmic disease and/or disorder, comprising administering to the eye of a subject in need thereof an effective amount of a drug-loaded micelle comprising self-assembled amphiphilic first nucleic acid molecules provided at the 3' or 5' end with a hydrophobic moiety and wherein at least one drug is attached to the first nucleic acid molecule via a hybridized second nucleic acid that is provided with the drug, wherein the hydrophobic moiety at the 3' or 5' end is formed by 2 to 6 contiguous hydrophobically-modified 2'-deoxyuridine nucleotides, wherein the hydrophobic moiety contains a hydrocarbon chain of 6 to 30 C-atoms, the content of modified 2'-deoxyuridine within the first nucleic acid molecule is about 30% or higher, and the nucleic acid molecule has at least 10 and less than 60 nucleotides.

5. The method according to claim 1, wherein said amphiphilic biopolymer is a nucleic acid molecule consisting of 10 to 20 nucleotides, wherein the hydrophobic moiety at the 3' or 5' end is formed by 2 to 6 contiguous hydrophobically-modified nucleotides.

6. The method according to claim 1, wherein the hydrocarbon chain is a straight C10-C20 alkyl chain.

7. The method according to claim 1, wherein the contiguous hydrophobically-modified nucleotides have the same hydrophobic groups.

8. The method according to claim 1, wherein the contiguous hydrophobically-modified nucleotides have distinct hydrophobic groups.

9. The method according to claim 1, wherein the micelle comprises a hydrophobic drug enclosed in the hydrophobic core of the micelle.

10. The method according to claim 1, wherein the hydrophilic moiety of at least one amphiphile is provided with the drug.

11. The method according to claim 10, wherein the hydrophilic moiety is a first nucleic acid and wherein the drug is attached to the hydrophilic moiety via a hybridized second nucleic acid provided with the drug.

12. The method according to claim 11, wherein the drug is covalently bound to said hybridized second nucleic acid.

13. The method according to claim 11, wherein the drug is bound to said hybridized second nucleic acid via an aptameric interaction.

14. The method of claim 1, wherein the drug is an ophthalmic drug selected from the group consisting of anti-glaucoma agents, anti-angiogenesis agents, anti-infective agents, nonsteroidal or steroidal anti-inflammatory agents, growth factors, immunosuppressant agents, anti-allergic agents, and a pro-drug form thereof.

15. The method of claim 1, wherein the drug is an aminoglycoside antibiotic.

16. The method of claim 15, wherein the antibiotic is neomycin, kanamycin or a derivative thereof.

17. The method of claim 14, wherein the drug is a prostaglandin.

18. The method of claim 17, wherein the prostaglandin is selected from the group consisting of latanoprost, bimatoprost, tafluprost, unoprostone and travoprost.

19. The method of claim 14, wherein the drug is an adrenergic agonist.

20. The method of claim 19, wherein the adrenergic agonist is apraclonidine or brimonidine.

* * * * *